US012734063B2

(12) United States Patent
Johannes et al.

(10) Patent No.: US 12,734,063 B2
(45) Date of Patent: Sep. 15, 2026

(54) APPARATUS AND METHODS FOR RECEIVING DISCHARGED URINE

(71) Applicant: PUREWICK CORPORATION, El Cajon, CA (US)

(72) Inventors: Ashley Marie Johannes, Statham, GA (US); Justin Wolfe, Lawrenceville, GA (US)

(73) Assignee: PUREWICK CORPORATION, Covington, GA (US)

( * ) Notice: Subject to any disclaimer, the term of this patent is extended or adjusted under 35 U.S.C. 154(b) by 498 days.

(21) Appl. No.: 17/757,311

(22) PCT Filed: Dec. 16, 2020

(86) PCT No.: PCT/US2020/065234
§ 371 (c)(1),
(2) Date: Jun. 14, 2022

(87) PCT Pub. No.: WO2021/126920
PCT Pub. Date: Jun. 24, 2021

(65) Prior Publication Data

US 2022/0370235 A1 Nov. 24, 2022

Related U.S. Application Data

(60) Provisional application No. 62/949,187, filed on Dec. 17, 2019.

(51) Int. Cl.
*A61F 5/453* (2006.01)
*A61F 5/44* (2006.01)

(52) U.S. Cl.
CPC ............ *A61F 5/453* (2013.01); *A61F 5/4408* (2013.01)

(58) Field of Classification Search
CPC .............................. A61F 5/453; A61F 5/4408
See application file for complete search history.

(56) References Cited

U.S. PATENT DOCUMENTS 670,602 A 3/1901 Baker
737,443 A 8/1903 Mooers
(Continued)

FOREIGN PATENT DOCUMENTS

AU 2018216821 A1 8/2019
AU 2021299304 A1 2/2023
(Continued)

OTHER PUBLICATIONS

US 9,908,683 B2, 03/2018, Sandhausen et al. (withdrawn)
(Continued)

*Primary Examiner* — Kai H Weng
*Assistant Examiner* — Katherine-Ph Minh Pham
(74) *Attorney, Agent, or Firm* — Ballard Spahr LLP

(57) ABSTRACT

A device suitable for collecting and transporting urine away from the body of a person may include a receptacle and an elongate member. The receptacle can define a volume and include one or more channels and a passage. The one or more channels can direct the flow of urine to a collection region proximal to the passage. The passage can be used to extract urine from the device by coupling a vacuum pump to the passage and applying a negative pressure. The elongate member can include a distal end and a proximal end. A curved portion of the elongate member can be formed between the distal and proximal ends. The curved portion can be positioned between the thighs of the user and proximal to a perineum of the user to retain the device in a fixed position relative to the user.

19 Claims, 7 Drawing Sheets

(56) References Cited

U.S. PATENT DOCUMENTS 976,883 A * 11/1910 Keagy .................. A61F 5/4553 600/574
1,015,905 A 1/1912 Northrop
1,032,841 A 7/1912 Koenig
1,178,644 A 4/1916 Johnson
1,229,423 A * 6/1917 Eckenrode ............. A61F 5/453 604/340
1,387,726 A 8/1921 Karge
1,742,080 A 12/1929 Jones
1,979,899 A 11/1934 Obrien et al.
2,241,010 A 5/1941 Chipley
2,262,772 A 11/1941 Peder
2,326,881 A 8/1943 Packer
2,379,346 A 6/1945 Farrell
2,485,555 A 10/1949 Bester
2,571,357 A 10/1951 Charles
2,613,670 A 10/1952 Edward
2,616,426 A 11/1952 Adele
2,644,234 A 7/1953 Earl
2,648,335 A 8/1953 Chambers
2,789,560 A 4/1957 Weimer
2,859,786 A 11/1958 Tupper
2,944,551 A 7/1960 Carl
2,968,046 A 1/1961 Duke
2,971,512 A 2/1961 Reinhardt
3,032,038 A 5/1962 Swinn
3,077,883 A 2/1963 Hill
3,087,938 A 4/1963 Hans et al.
3,114,916 A 12/1963 Hadley
3,169,528 A 2/1965 Knox et al.
3,171,506 A 3/1965 Therkel
3,175,719 A 3/1965 Herndon
3,194,238 A 7/1965 Breece
3,198,994 A 8/1965 Hildebrandt et al.
3,221,742 A 12/1965 Egon
3,312,221 A 4/1967 Overment
3,312,981 A 4/1967 Mcguire et al.
3,349,768 A 10/1967 Keane
3,362,590 A 1/1968 Gene
3,366,116 A 1/1968 Huck
3,368,564 A 2/1968 Selix
3,398,848 A 8/1968 Donovan
3,400,717 A 9/1968 Bruce et al.
3,406,688 A 10/1968 Bruce
3,424,163 A 1/1969 Gravdahl
3,425,471 A 2/1969 Yates
3,434,565 A 3/1969 Fischer
3,447,536 A * 6/1969 Snyder ................... A61F 5/453 604/348
3,511,241 A 5/1970 Lee
3,512,185 A 5/1970 Ellis
3,520,300 A 7/1970 Flower
3,528,423 A 9/1970 Lee
3,608,552 A 9/1971 Broerman
3,613,123 A 10/1971 Langstrom
3,648,700 A 3/1972 Warner
3,651,810 A 3/1972 Ormerod
3,661,155 A 5/1972 Lindan
3,683,918 A 8/1972 Pizzella
3,699,815 A 10/1972 Holbrook
3,721,243 A 3/1973 Greth et al.
3,726,277 A 4/1973 Hirschman
3,742,952 A 7/1973 Magers et al.
3,742,953 A 7/1973 Lee
3,757,355 A 9/1973 Allen et al.
3,788,324 A 1/1974 Lim
3,843,016 A 10/1974 Bornhorst et al.
3,863,638 A 2/1975 Rogers et al.
3,863,798 A 2/1975 Kurihara et al.
3,864,759 A 2/1975 Horiuchi
3,865,109 A 2/1975 Elmore et al.
3,881,486 A 5/1975 Fenton
3,881,489 A 5/1975 Hartwell
3,915,189 A 10/1975 Holbrook et al.
3,931,650 A 1/1976 Miller
3,964,786 A 6/1976 Mashuda
3,998,228 A 12/1976 Poidomani
3,999,550 A 12/1976 Martin
4,006,793 A 2/1977 Robinson
4,015,604 A 4/1977 Csillag
4,020,843 A 5/1977 Kanall
4,022,211 A 5/1977 Timmons et al.
4,022,213 A 5/1977 Stein
4,027,776 A 6/1977 Douglas
4,031,897 A 6/1977 Graetz
4,042,337 A 8/1977 Griffith
4,064,962 A 12/1977 Hunt
4,069,817 A 1/1978 Fenole et al.
4,084,589 A 4/1978 Kulvi
4,096,897 A 6/1978 Cammarata
4,116,197 A 9/1978 Bermingham
4,140,739 A 2/1979 Cotten
4,180,178 A 12/1979 Turner
4,187,953 A 2/1980 Turner
4,194,508 A 3/1980 Anderson
4,197,849 A 4/1980 Bostick
4,200,102 A 4/1980 Duhamel et al.
4,202,058 A 5/1980 Anderson
4,203,503 A 5/1980 Bertotti et al.
4,209,076 A 6/1980 Bertotti et al.
4,223,677 A 9/1980 Anderson
4,233,025 A 11/1980 Larson et al.
4,233,978 A 11/1980 Hickey
4,246,901 A 1/1981 Frosch et al.
4,253,542 A 3/1981 Ruspa et al.
4,257,418 A 3/1981 Hessner
4,270,539 A 6/1981 Frosch et al.
4,280,498 A 7/1981 Jensen
4,281,655 A 8/1981 Terauchi
4,292,916 A 10/1981 Bradley et al.
4,330,239 A 5/1982 Gannaway
4,345,341 A 8/1982 Saito
4,349,029 A 9/1982 Mott
4,352,356 A 10/1982 Tong
4,356,012 A 10/1982 Hofstetter
4,360,933 A 11/1982 Kimura et al.
4,365,363 A 12/1982 Windauer
4,375,841 A 3/1983 Vielbig
4,387,726 A 6/1983 Denard
4,403,991 A 9/1983 Hill
4,421,511 A 12/1983 Steer et al.
4,425,130 A 1/1984 Desmarais
4,446,986 A 5/1984 Bowen et al.
4,453,938 A 6/1984 Brendling
4,457,314 A 7/1984 Knowles
4,457,758 A 7/1984 Norton
4,476,879 A 10/1984 Jackson
4,512,771 A 4/1985 Norton
4,526,688 A 7/1985 Schmidt et al.
4,528,703 A 7/1985 Kraus
4,533,354 A 8/1985 Jensen
4,533,357 A 8/1985 Hall
D280,438 S 9/1985 Wendt
4,551,141 A 11/1985 Mcneil
4,553,968 A 11/1985 Komis
4,568,341 A 2/1986 Mitchell et al.
4,581,026 A 4/1986 Schneider
4,583,983 A 4/1986 Einhorn et al.
4,589,516 A 5/1986 Inoue et al.
4,601,716 A 7/1986 Smith
4,610,675 A 9/1986 Triunfol
4,620,333 A 11/1986 Ritter
4,626,250 A 12/1986 Schneider
4,627,846 A 12/1986 Ternstroem
4,631,061 A 12/1986 Martin
4,650,477 A 3/1987 Johnson
4,655,754 A 4/1987 Richmond et al.
4,656,675 A 4/1987 Fajnsztajn
4,681,570 A 7/1987 Dalton
4,681,572 A 7/1987 Tokarz et al.
4,681,577 A 7/1987 Stern et al.
4,692,160 A 9/1987 Nussbaumer
4,707,864 A 11/1987 Ikematsu et al.
4,713,065 A 12/1987 Koot

(56) References Cited

U.S. PATENT DOCUMENTS 4,713,066 A 12/1987 Komis
4,723,953 A 2/1988 Pratt et al.
4,735,841 A 4/1988 Sourdet
4,743,236 A 5/1988 Manschot
4,747,166 A 5/1988 Kuntz
4,752,944 A 6/1988 Conrads et al.
4,759,753 A 7/1988 Schneider et al.
4,769,215 A 9/1988 Ehrenkranz
4,771,484 A 9/1988 Mozell
4,772,280 A 9/1988 Rooyakkers
4,775,458 A 10/1988 Forester
4,784,654 A 11/1988 Beecher
4,790,830 A 12/1988 Hamacher
4,790,835 A 12/1988 Elias
4,791,686 A 12/1988 Taniguchi et al.
4,795,449 A 1/1989 Schneider et al.
4,798,603 A 1/1989 Meyer et al.
4,799,928 A 1/1989 Crowley
4,804,377 A 2/1989 Hanifl et al.
4,812,053 A 3/1989 Bhattacharjee
4,813,943 A 3/1989 Smith
4,820,291 A 4/1989 Terauchi et al.
4,820,297 A 4/1989 Kaufman et al.
4,841,728 A 6/1989 Jean et al.
4,846,818 A 7/1989 Keldahl et al.
4,846,819 A 7/1989 Welch
4,846,824 A 7/1989 Lassen et al.
4,846,909 A 7/1989 Klug et al.
4,865,595 A 9/1989 Heyden
4,880,417 A 11/1989 Yabrov et al.
4,882,794 A 11/1989 Stewart
4,883,465 A 11/1989 Brennan
4,886,498 A 12/1989 Newton
4,886,508 A 12/1989 Washington
4,886,509 A 12/1989 Mattsson
4,889,532 A 12/1989 Metz et al.
4,889,533 A 12/1989 Beecher
4,890,691 A 1/1990 Ching-Ho
4,895,140 A 1/1990 Bellak
4,903,254 A 2/1990 Haas
4,904,248 A 2/1990 Vaillancourt
4,905,692 A 3/1990 More
4,911,262 A 3/1990 Tani et al.
4,930,997 A 6/1990 Bennett
4,936,838 A 6/1990 Cross et al.
4,950,262 A 8/1990 Takagi
4,955,922 A 9/1990 Terauchi
4,957,487 A 9/1990 Gerow
4,965,460 A 10/1990 Tanaka et al.
4,986,823 A 1/1991 Anderson et al.
4,987,849 A 1/1991 Sherman
5,002,541 A 3/1991 Conkling et al.
5,004,463 A 4/1991 Nigay
5,013,308 A 5/1991 Sullivan et al.
5,031,248 A 7/1991 Kemper
5,045,077 A 9/1991 Blake
5,045,283 A 9/1991 Patel
5,049,144 A 9/1991 Payton
5,053,339 A 10/1991 Patel
5,057,092 A 10/1991 Webster
5,058,088 A 10/1991 Haas et al.
5,071,347 A 12/1991 Mcguire
5,078,707 A 1/1992 Peter
5,084,037 A 1/1992 Barnett
5,100,396 A 3/1992 Zamierowski
5,102,404 A 4/1992 Goldberg et al.
5,112,324 A 5/1992 Wallace
5,134,994 A 8/1992 Say
5,137,033 A 8/1992 Norton
5,147,301 A 9/1992 Ruvio
5,176,667 A 1/1993 Debring
5,195,997 A 3/1993 Carns
5,196,654 A 3/1993 Diflora et al.
5,199,444 A 4/1993 Wheeler
5,203,699 A 4/1993 Mcguire
5,244,458 A 9/1993 Takasu
5,246,454 A 9/1993 Peterson
5,267,988 A 12/1993 Farkas
5,275,307 A 1/1994 Freese
5,282,795 A 2/1994 Finney
5,294,983 A 3/1994 Ersoz et al.
5,295,979 A 3/1994 DeLaurentis et al.
5,295,983 A 3/1994 Kubo
5,300,052 A 4/1994 Kubo
5,304,749 A 4/1994 Crandell
5,312,383 A 5/1994 Kubalak
5,318,550 A 6/1994 Cermak et al.
5,330,457 A 7/1994 Cohen
5,330,459 A 7/1994 Lavon et al.
5,334,174 A 8/1994 Street
5,334,176 A 8/1994 Buenger et al.
5,340,840 A 8/1994 Park et al.
5,382,244 A 1/1995 Telang
5,397,315 A 3/1995 Schmidt et al.
5,409,014 A 4/1995 Napoli et al.
5,409,475 A 4/1995 Steer
5,411,495 A 5/1995 Willingham
5,423,784 A 6/1995 Metz
5,423,788 A 6/1995 Rollins et al.
5,437,836 A 8/1995 Yamada
5,456,246 A 10/1995 Schmieding et al.
5,466,229 A 11/1995 Elson et al.
5,478,334 A 12/1995 Bernstein
5,499,977 A 3/1996 Marx
5,543,042 A 8/1996 Filan et al.
D373,928 S 9/1996 Green
5,582,604 A 12/1996 Ahr et al.
5,592,950 A 1/1997 Kopelowicz
5,593,389 A 1/1997 Chang
5,605,161 A 2/1997 Cross
5,614,699 A 3/1997 Yashiro et al.
5,618,277 A 4/1997 Goulter
5,628,735 A 5/1997 Skow
5,632,736 A 5/1997 Block
5,636,643 A 6/1997 Argenta et al.
5,637,104 A 6/1997 Ball et al.
5,662,633 A 9/1997 Doak et al.
5,674,212 A 10/1997 Osborn et al.
5,678,564 A 10/1997 Lawrence et al.
5,678,654 A 10/1997 Uzawa
5,681,297 A 10/1997 Hashimoto et al.
5,687,429 A 11/1997 Rahlff
5,695,485 A 12/1997 Duperret et al.
5,700,254 A 12/1997 Mcdowall et al.
5,701,612 A 12/1997 Daneshvar
5,705,777 A 1/1998 Flanigan et al.
5,735,835 A 4/1998 Holland
5,735,837 A 4/1998 Ishikawa
5,752,944 A 5/1998 Dann et al.
5,763,333 A 6/1998 Suzuki et al.
5,772,644 A 6/1998 Bark et al.
5,792,132 A 8/1998 Garcia
5,827,243 A 10/1998 Palestrant
5,827,247 A 10/1998 Kay
5,827,250 A 10/1998 Fujioka et al.
5,827,257 A 10/1998 Fujioka et al.
D401,699 S 11/1998 Herchenbach et al.
5,859,393 A 1/1999 Cummins et al.
5,865,378 A 2/1999 Hollinshead et al.
5,873,869 A 2/1999 Hammons et al.
5,876,393 A 3/1999 Ahr et al.
5,887,291 A 3/1999 Bellizzi
5,891,125 A 4/1999 Plumley
5,894,608 A 4/1999 Birbara
5,895,349 A 4/1999 Tihon
D409,303 S 5/1999 Oepping
5,911,222 A 6/1999 Lawrence et al.
5,956,782 A 9/1999 Olguin
5,957,904 A 9/1999 Holland
5,968,026 A 10/1999 Osborn et al.
5,972,505 A 10/1999 Phillips et al.
6,007,526 A 12/1999 Passalaqua et al.
6,039,060 A 3/2000 Rower
6,050,983 A 4/2000 Moore et al.

(56) References Cited

U.S. PATENT DOCUMENTS 6,059,762 A 5/2000 Boyer et al.
6,063,064 A 5/2000 Tuckey et al.
6,098,625 A 8/2000 Winkler
6,105,174 A 8/2000 Karlsten et al.
6,113,582 A 9/2000 Dwork
6,117,163 A 9/2000 Bierman
6,123,398 A 9/2000 Arai et al.
6,129,718 A 10/2000 Wada et al.
6,131,964 A 10/2000 Sareshwala
6,152,902 A 11/2000 Christian et al.
6,164,569 A 12/2000 Hollinshead et al.
6,177,606 B1 1/2001 Etheredge et al.
6,209,142 B1 4/2001 Mattsson et al.
6,220,050 B1 4/2001 Cooksey
6,244,311 B1 6/2001 Hand et al.
6,248,096 B1 6/2001 Dwork et al.
6,263,887 B1 7/2001 Dunn
6,283,246 B1 9/2001 Nishikawa
6,296,627 B1 10/2001 Edwards
6,311,339 B1 11/2001 Kraus
6,316,688 B1 11/2001 Hammons et al.
6,336,919 B1 1/2002 Davis et al.
6,338,729 B1 1/2002 Wada et al.
6,352,525 B1 3/2002 Wakabayashi
6,394,988 B1 * 5/2002 Hashimoto ............. A61G 9/00 604/327
6,395,956 B1 5/2002 Glasgow et al.
6,398,742 B1 6/2002 Kim
6,406,463 B1 6/2002 Brown
6,409,712 B1 6/2002 Dutari et al.
6,415,888 B2 7/2002 An et al.
6,416,500 B1 7/2002 Wada et al.
6,423,045 B1 7/2002 Wise et al.
6,428,521 B1 8/2002 Droll
6,428,522 B1 8/2002 Dipalma et al.
6,446,454 B1 9/2002 Lee et al.
6,461,340 B1 10/2002 Lenker et al.
6,467,570 B1 10/2002 Herold
6,475,198 B1 11/2002 Lipman et al.
6,479,726 B1 11/2002 Cole et al.
6,491,673 B1 12/2002 Palumbo et al.
6,508,794 B1 1/2003 Palumbo et al.
6,524,292 B1 2/2003 Dipalma et al.
6,526,603 B1 3/2003 Murphy
6,540,729 B1 4/2003 Wada et al.
6,547,771 B2 4/2003 Robertson et al.
6,551,293 B1 4/2003 Mitchell
6,569,133 B2 5/2003 Cheng et al.
D476,518 S 7/2003 Doppelt
6,592,560 B2 7/2003 Snyder et al.
6,610,038 B1 8/2003 Dipalma et al.
6,618,868 B2 9/2003 Minnick
6,620,142 B1 9/2003 Flueckiger
6,629,651 B1 10/2003 Male et al.
6,635,037 B1 10/2003 Bennett
6,635,038 B2 10/2003 Scovel
6,652,495 B1 11/2003 Walker
6,666,850 B1 12/2003 Ahr et al.
6,685,684 B1 2/2004 Falconer
6,695,828 B1 2/2004 Dipalma et al.
6,699,174 B1 3/2004 Bennett
6,700,034 B1 3/2004 Lindsay et al.
6,702,793 B1 3/2004 Sweetser et al.
6,706,027 B2 3/2004 Harvie et al.
6,732,384 B2 5/2004 Scott
6,736,977 B1 5/2004 Hall et al.
6,740,066 B2 5/2004 Wolff et al.
6,764,477 B1 7/2004 Chen et al.
6,783,519 B2 8/2004 Samuelsson
6,796,974 B2 9/2004 Palumbo et al.
6,814,547 B2 11/2004 Childers et al.
6,848,719 B2 2/2005 Rowley
6,849,065 B2 2/2005 Schmidt et al.
6,857,137 B2 2/2005 Otto
6,885,690 B2 4/2005 Aggerstam et al.
6,888,044 B2 5/2005 Fell et al.
6,893,425 B2 5/2005 Dunn et al.
6,912,737 B2 7/2005 Ernest et al.
6,918,899 B2 7/2005 Harvie
6,979,324 B2 12/2005 Bybordi et al.
7,018,366 B2 3/2006 Easter
7,066,411 B2 6/2006 Male et al.
7,087,043 B2 8/2006 Dolan
7,122,023 B1 10/2006 Hinoki
7,125,399 B2 10/2006 Miskie
7,131,964 B2 11/2006 Harvie
7,135,012 B2 11/2006 Harvie
7,141,043 B2 11/2006 Harvie
D533,972 S 12/2006 La
7,160,273 B2 1/2007 Greter et al.
7,166,092 B2 1/2007 Elson et al.
7,171,699 B2 2/2007 Ernest et al.
7,171,871 B2 2/2007 Kozak
7,179,951 B2 2/2007 Krishnaswamy-Mirle et al.
7,181,781 B1 2/2007 Trabold et al.
7,186,245 B1 3/2007 Cheng et al.
7,192,424 B2 3/2007 Cooper
7,219,764 B1 5/2007 Forbes
7,220,250 B2 5/2007 Suzuki et al.
D562,975 S 2/2008 Otto
7,335,189 B2 2/2008 Harvie
7,358,282 B2 4/2008 Krueger et al.
7,390,320 B2 6/2008 Machida et al.
7,438,706 B2 10/2008 Koizumi et al.
7,488,310 B2 2/2009 Yang
7,491,194 B1 2/2009 Oliwa
D591,106 S 4/2009 Dominique et al.
7,513,381 B2 4/2009 Heng et al.
7,520,872 B2 4/2009 Biggie et al.
D593,801 S 6/2009 Wilson et al.
7,540,364 B2 6/2009 Sanderson
7,549,511 B2 6/2009 Marocco
7,549,512 B2 6/2009 Newberry
7,585,293 B2 9/2009 Vermaak
7,588,560 B1 9/2009 Dunlop
7,637,905 B2 12/2009 Saadat et al.
7,658,730 B2 2/2010 Conley
7,665,359 B2 2/2010 Barber
7,682,347 B2 3/2010 Parks et al.
7,687,004 B2 3/2010 Allen
7,695,459 B2 4/2010 Gilbert et al.
7,695,460 B2 4/2010 Wada et al.
7,699,818 B2 4/2010 Gilbert
7,699,831 B2 4/2010 Bengtson et al.
7,722,584 B2 5/2010 Tanaka et al.
7,727,206 B2 6/2010 Gorres
7,740,620 B2 6/2010 Gilbert et al.
7,749,205 B2 7/2010 Tazoe et al.
7,755,497 B2 7/2010 Wada et al.
7,766,887 B2 8/2010 Burns et al.
7,803,144 B1 9/2010 Vollrath
D625,407 S 10/2010 Koizumi et al.
7,806,879 B2 10/2010 Brooks et al.
7,811,272 B2 10/2010 Lindsay et al.
7,815,067 B2 10/2010 Matsumoto et al.
7,833,169 B2 11/2010 Hannon
7,857,806 B2 12/2010 Karpowicz et al.
7,866,942 B2 1/2011 Harvie
7,871,385 B2 1/2011 Levinson et al.
7,875,010 B2 1/2011 Frazier et al.
7,901,389 B2 3/2011 Mombrinie
7,927,320 B2 4/2011 Goldwasser et al.
7,927,321 B2 4/2011 Marland
7,931,634 B2 4/2011 Swiecicki et al.
7,939,706 B2 5/2011 Okabe et al.
7,946,443 B2 5/2011 Stull et al.
7,947,025 B2 5/2011 Buglino et al.
7,963,419 B2 6/2011 Burney et al.
7,976,519 B2 7/2011 Bubb et al.
7,981,087 B2 7/2011 Gesler, III
7,993,318 B2 8/2011 Olsson et al.
8,015,627 B2 9/2011 Baker et al.
8,016,071 B1 9/2011 Martinus et al.
8,028,460 B2 10/2011 Williams

(56) References Cited

U.S. PATENT DOCUMENTS 8,047,398 B2 11/2011 Dimartino et al.
8,083,094 B2 12/2011 Caulfield et al.
8,128,608 B2 3/2012 Thevenin
8,167,860 B1 5/2012 Siegel
8,181,651 B2 5/2012 Pinel
8,181,819 B2 5/2012 Burney et al.
8,211,063 B2 7/2012 Bierman et al.
8,221,369 B2 7/2012 Parks et al.
8,241,262 B2 8/2012 Mahnensmith
8,277,426 B2 10/2012 Wilcox et al.
8,287,508 B1 10/2012 Sanchez
8,303,554 B2 11/2012 Tsai et al.
8,322,565 B2 12/2012 Caulfield et al.
8,337,477 B2 12/2012 Parks et al.
D674,241 S 1/2013 Bickert et al.
8,343,122 B2 1/2013 Gorres
8,343,125 B2 1/2013 Kawazoe et al.
8,353,074 B2 1/2013 Krebs
8,353,886 B2 1/2013 Bester et al.
D676,241 S 2/2013 Merrill
8,388,587 B1 3/2013 Gmuer et al.
8,388,588 B2 3/2013 Wada et al.
D679,807 S 4/2013 Burgess et al.
8,425,482 B2 4/2013 Khoubnazar
8,434,586 B2 5/2013 Pawelski et al.
8,449,510 B2 5/2013 Martini et al.
D684,260 S 6/2013 Lund et al.
8,470,230 B2 6/2013 Caulfield et al.
8,479,941 B2 7/2013 Matsumoto et al.
8,479,949 B2 7/2013 Henkel
8,500,719 B1 8/2013 Simpson et al.
8,512,301 B2 8/2013 Ma
8,529,530 B2 9/2013 Koch et al.
8,535,284 B2 9/2013 Joder et al.
8,546,639 B2 10/2013 Wada et al.
8,551,062 B2 10/2013 Kay
8,551,075 B2 10/2013 Bengtson
8,568,376 B2 10/2013 Delattre et al.
D694,404 S 11/2013 Burgess et al.
8,585,683 B2 11/2013 Bengtson et al.
8,652,112 B2 2/2014 Johannison et al.
8,669,412 B2 3/2014 Fernkvist et al.
D702,973 S 4/2014 Norland et al.
8,702,667 B1 4/2014 Johnson
8,703,032 B2 4/2014 Menon et al.
D704,330 S 5/2014 Cicatelli
D704,510 S 5/2014 Mason et al.
D705,423 S 5/2014 Walsh Cutler
D705,926 S 5/2014 Burgess et al.
8,714,394 B2 5/2014 Wulf
8,715,267 B2 5/2014 Bengtson et al.
8,740,852 B2 6/2014 Aviles
8,757,425 B2 6/2014 Copeland
8,777,032 B2 7/2014 Biesecker et al.
8,808,260 B2 8/2014 Koch et al.
8,864,730 B2 10/2014 Conway et al.
8,881,923 B2 11/2014 Higginson
8,882,731 B2 11/2014 Suzuki et al.
8,936,585 B2 1/2015 Carson et al.
D729,581 S 5/2015 Boroski
9,028,460 B2 5/2015 Medeiros
9,056,698 B2 6/2015 Noer
9,078,792 B2 7/2015 Ruiz
9,145,879 B2 9/2015 Pirovano et al.
9,173,602 B2 11/2015 Gilbert
9,173,799 B2 11/2015 Tanimoto et al.
9,187,220 B2 11/2015 Biesecker et al.
9,199,772 B2 12/2015 Krippendorf
9,233,020 B2 1/2016 Matsumiya
9,248,058 B2 2/2016 Conway et al.
9,308,118 B1 4/2016 Dupree et al.
9,309,029 B2 4/2016 Incorvia et al.
9,333,281 B2 5/2016 Giezendanner et al.
9,381,108 B2 7/2016 Longoni et al.
9,382,047 B2 7/2016 Schmidtner et al.
9,402,424 B2 8/2016 Roy
9,415,191 B2 8/2016 Aviles
9,456,937 B2 10/2016 Ellis
9,480,595 B2 11/2016 Baham et al.
9,517,865 B2 12/2016 Albers et al.
D777,941 S 1/2017 Piramoon
9,533,806 B2 1/2017 Ding et al.
9,550,611 B2 1/2017 Hodge
9,555,930 B2 1/2017 Campbell et al.
9,623,159 B2 4/2017 Locke
D789,522 S 6/2017 Burgess et al.
9,687,849 B2 6/2017 Bruno et al.
9,694,949 B2 7/2017 Hendricks et al.
9,709,048 B2 7/2017 Kinjo
9,713,547 B2 7/2017 Lee et al.
9,732,754 B2 8/2017 Huang et al.
9,737,433 B2 8/2017 Joh
9,752,564 B2 9/2017 Arceno et al.
9,788,992 B2 10/2017 Harvie
D804,907 S 12/2017 Sandoval
9,868,564 B2 1/2018 Mcgirr et al.
D814,239 S 4/2018 Arora
D817,484 S 5/2018 Lafond
9,968,908 B2 5/2018 Ladrech et al.
10,010,393 B1 7/2018 Nguyen et al.
10,037,640 B2 7/2018 Gordon
10,058,470 B2 8/2018 Phillips
10,098,990 B2 10/2018 Koch et al.
D835,264 S 12/2018 Mozzicato et al.
D835,779 S 12/2018 Mozzicato et al.
D840,533 S 2/2019 Mozzicato et al.
D840,534 S 2/2019 Mozzicato et al.
10,225,376 B2 3/2019 Perez Martinez
10,226,376 B2 3/2019 Sanchez et al.
10,258,517 B1 4/2019 Maschino et al.
D848,612 S 5/2019 Mozzicato et al.
10,307,305 B1 6/2019 Hodges
10,335,121 B2 7/2019 Desai
D856,512 S 8/2019 Cowart et al.
10,376,406 B2 8/2019 Newton
10,376,407 B2 8/2019 Newton
10,390,989 B2 8/2019 Sanchez et al.
D858,144 S 9/2019 Fu
10,406,039 B2 9/2019 Mllarreal
10,407,222 B2 9/2019 Allen
10,478,356 B2 11/2019 Griffin
10,500,108 B1 12/2019 Maschino et al.
10,502,198 B2 12/2019 Stumpf et al.
10,538,366 B2 1/2020 Pentelovitch et al.
10,569,938 B2 2/2020 Zhao et al.
10,577,156 B2 3/2020 Dagnelie et al.
RE47,930 E 4/2020 Cho
10,618,721 B2 4/2020 Vazin
D884,390 S 5/2020 Wang
10,669,079 B2 6/2020 Freedman et al.
D892,315 S 8/2020 Airy
10,730,672 B2 8/2020 Bertram et al.
10,737,848 B2 8/2020 Philip et al.
10,765,854 B2 9/2020 Law et al.
10,766,670 B2 9/2020 Kittmann
10,799,386 B1 10/2020 Harrison
10,806,623 B2 10/2020 VanMiddendorp et al.
10,806,642 B2 10/2020 Tagomori et al.
D901,214 S 11/2020 Hu
10,849,799 B2 12/2020 Nishikawa et al.
10,857,025 B2 12/2020 Davis et al.
10,865,017 B1 12/2020 Cowart et al.
10,889,412 B2 1/2021 West et al.
10,913,581 B2 2/2021 Stahlecker
D912,244 S 3/2021 Rehm et al.
10,952,889 B2 3/2021 Newton et al.
10,973,378 B2 4/2021 Ryu et al.
10,973,678 B2 4/2021 Newton et al.
10,974,874 B2 4/2021 Ragias et al.
11,000,401 B2 5/2021 Ecklund et al.
11,002,165 B2 5/2021 Poulin
D923,365 S 6/2021 Wang
11,020,567 B2 6/2021 Rule et al.
11,026,829 B2 6/2021 Harvie

(56) References Cited

U.S. PATENT DOCUMENTS 11,027,900 B2 6/2021 Liu
11,045,346 B2 6/2021 Argent et al.
D928,946 S 8/2021 Sanchez et al.
11,090,183 B2 8/2021 Sanchez et al.
11,160,695 B2 11/2021 Febo et al.
11,160,697 B2 11/2021 Maschino et al.
11,168,420 B2 11/2021 Kinugasa et al.
11,179,506 B2 11/2021 Barr et al.
11,199,116 B2 12/2021 Ostromecki et al.
11,207,206 B2 12/2021 Sharma et al.
11,226,376 B2 1/2022 Yamauchi et al.
11,253,389 B2 2/2022 Sharma et al.
11,253,407 B2 2/2022 Miao et al.
11,326,586 B2 5/2022 Milner et al.
11,369,508 B2 6/2022 Ecklund et al.
11,369,524 B2 6/2022 Hubbard et al.
11,376,152 B2 7/2022 Sanchez et al.
11,382,786 B2 7/2022 Sanchez et al.
11,382,788 B2 7/2022 Hjorth et al.
11,389,318 B2 7/2022 Radl et al.
11,395,871 B2 7/2022 Radl et al.
11,399,990 B2 8/2022 Suyama
11,426,303 B2 8/2022 Davis et al.
11,504,265 B2 11/2022 Godinez et al.
11,529,252 B2 12/2022 Glithero et al.
11,547,788 B2 1/2023 Radl et al.
11,806,266 B2 11/2023 Sanchez et al.
11,813,189 B2 11/2023 Hussey et al.
11,839,567 B2 12/2023 Davis et al.
D1,010,109 S 1/2024 Ecklund et al.
11,857,716 B2 1/2024 Lee et al.
11,865,030 B2 1/2024 Davis et al.
11,890,221 B2 2/2024 Ulreich et al.
11,911,160 B2 2/2024 Woodard et al.
11,925,575 B2 3/2024 Newton
11,938,053 B2 3/2024 Austermann et al.
11,944,740 B2 4/2024 Hughett et al.
11,994,122 B2 5/2024 Bodain
11,998,475 B2 6/2024 Becker et al.
12,023,457 B2 7/2024 Mann et al.
12,042,422 B2 7/2024 Davis et al.
D1,038,385 S 8/2024 Ecklund et al.
12,064,372 B2 8/2024 Godinez et al.
12,070,432 B2 8/2024 Tourchak et al.
12,090,083 B2 9/2024 Ecklund et al.
12,121,468 B2 10/2024 Sanchez et al.
12,133,813 B2 11/2024 Ulreich et al.
12,138,195 B2 11/2024 Alder et al.
12,186,229 B2 1/2025 Davis et al.
12,193,962 B2 1/2025 Newton et al.
12,245,966 B2 3/2025 Newton
12,274,638 B2 4/2025 Spector
12,350,190 B2 7/2025 Hughett, Sr. et al.
2001/0037097 A1 11/2001 Cheng et al.
2001/0037098 A1 11/2001 Snyder
2001/0054426 A1 12/2001 Knudson et al.
2002/0019614 A1 2/2002 Woon
2002/0026161 A1 2/2002 Grundke
2002/0026163 A1 2/2002 Grundke
2002/0042945 A1 4/2002 Sands
2002/0087131 A1 7/2002 Wolff et al.
2002/0091364 A1 7/2002 Prabhakar
2002/0189992 A1 12/2002 Schmidt et al.
2002/0193760 A1 12/2002 Thompson
2002/0193762 A1 12/2002 Suydam
2003/0004436 A1 1/2003 Schmidt et al.
2003/0032931 A1 2/2003 Grundke et al.
2003/0032944 A1 2/2003 Cawood
2003/0073964 A1 4/2003 Palumbo et al.
2003/0074724 A1 4/2003 Sands
2003/0120178 A1 6/2003 Heki
2003/0129178 A1 7/2003 Wegman et al.
2003/0157859 A1 8/2003 Ishikawa
2003/0181880 A1 9/2003 Schwartz
2003/0195484 A1 10/2003 Harvie
2003/0204173 A1 10/2003 Burns et al.
2003/0233079 A1 12/2003 Parks et al.
2004/0006321 A1 1/2004 Cheng et al.
2004/0015141 A1 1/2004 Cheng et al.
2004/0056122 A1 3/2004 Male et al.
2004/0084465 A1 5/2004 Luburic
2004/0127872 A1 7/2004 Petryk et al.
2004/0128749 A1 7/2004 Scott
2004/0143229 A1 7/2004 Easter
2004/0147863 A1 7/2004 Diaz et al.
2004/0147894 A1 7/2004 Mizutani et al.
2004/0147895 A1 7/2004 Mizutani et al.
2004/0158221 A1 8/2004 Mizutani et al.
2004/0176731 A1 9/2004 Cheng et al.
2004/0176746 A1 9/2004 Forral
2004/0181201 A1 9/2004 Mizutani et al.
2004/0187200 A1 9/2004 Otto et al.
2004/0191919 A1 9/2004 Unger et al.
2004/0194792 A1 10/2004 Zhuang et al.
2004/0200936 A1 10/2004 Opperthauser
2004/0207530 A1 10/2004 Nielsen
2004/0236292 A1 11/2004 Tazoe et al.
2004/0243075 A1 12/2004 Harvie
2004/0254547 A1 12/2004 Okabe et al.
2005/0010182 A1 1/2005 Parks et al.
2005/0010197 A1 1/2005 Lau et al.
2005/0033248 A1 2/2005 Machida et al.
2005/0065471 A1 3/2005 Kuntz
2005/0070861 A1 3/2005 Okabe et al.
2005/0070862 A1 3/2005 Tazoe et al.
2005/0082300 A1 4/2005 Modrell et al.
2005/0097662 A1 5/2005 Leimkuhler et al.
2005/0101924 A1 5/2005 Elson et al.
2005/0119630 A1 6/2005 Harvie
2005/0131361 A1 6/2005 Miskie
2005/0137557 A1 6/2005 Swiecicki et al.
2005/0137560 A1 6/2005 Mizutani et al.
2005/0137561 A1 6/2005 Mizutani et al.
2005/0148984 A1 7/2005 Lindsay et al.
2005/0154360 A1 7/2005 Harvie
2005/0177070 A1 8/2005 Levinson et al.
2005/0197639 A1 9/2005 Mombrinie
2005/0197645 A1 9/2005 Karpowicz et al.
2005/0215969 A1 9/2005 Mizutani et al.
2005/0273069 A1 12/2005 Mizutani et al.
2005/0273920 A1 12/2005 Marinas
2005/0277903 A1 12/2005 Mizutani et al.
2005/0277904 A1 12/2005 Chase et al.
2005/0279359 A1 12/2005 Leblanc et al.
2006/0004332 A1 1/2006 Marx
2006/0005307 A1 1/2006 Arguelles
2006/0015080 A1 1/2006 Mahnensmith
2006/0015081 A1 1/2006 Suzuki et al.
2006/0016778 A1 1/2006 Park
2006/0069359 A1 3/2006 Dipalma et al.
2006/0079854 A1 4/2006 Kay et al.
2006/0100596 A1 5/2006 Miskie
2006/0111648 A1 5/2006 Vermaak
2006/0113334 A1 6/2006 Mikhail et al.
2006/0155214 A1 7/2006 Wightman
2006/0166350 A1 7/2006 Lowe et al.
2006/0171997 A1 8/2006 Gruenbacher et al.
2006/0180566 A1 8/2006 Mataya
2006/0200102 A1 9/2006 Cooper
2006/0229575 A1 10/2006 Boiarski
2006/0229576 A1 10/2006 Conway et al.
2006/0231648 A1 10/2006 Male et al.
2006/0235266 A1 10/2006 Nan
2006/0235359 A1 10/2006 Marland
2006/0241553 A1 10/2006 Harvie
2006/0269439 A1 11/2006 White
2006/0277670 A1 12/2006 Baker et al.
2007/0006368 A1 1/2007 Key et al.
2007/0010797 A1 1/2007 Nishtala et al.
2007/0016152 A1 1/2007 Karpowicz et al.
2007/0025886 A1 2/2007 Yong
2007/0032765 A1* 2/2007 Honda .................... A61F 5/451
604/347
2007/0038194 A1 2/2007 Wada et al.

(56) References Cited

U.S. PATENT DOCUMENTS

2007/0055209 A1 3/2007 Patel et al.
2007/0073252 A1 3/2007 Forgrave
2007/0117880 A1 5/2007 Elson et al.
2007/0118993 A1 5/2007 Bates
2007/0135786 A1 6/2007 Schmidt et al.
2007/0137718 A1 6/2007 Rushlander et al.
2007/0149935 A1 6/2007 Dirico
2007/0191804 A1 8/2007 Coley
2007/0203464 A1 8/2007 Green et al.
2007/0214553 A1 9/2007 Carromba et al.
2007/0225663 A1 9/2007 Watt et al.
2007/0225666 A1 9/2007 Otto
2007/0225668 A1 9/2007 Otto
2007/0266486 A1 11/2007 Ramirez
2007/0270716 A1 11/2007 Wu et al.
2007/0282309 A1 12/2007 Bengtson et al.
2008/0004576 A1 1/2008 Tanaka et al.
2008/0015526 A1 1/2008 Reiner et al.
2008/0015527 A1 1/2008 House
2008/0033386 A1 2/2008 Okabe et al.
2008/0041869 A1 2/2008 Backaert
2008/0077099 A1 3/2008 House
2008/0091153 A1 4/2008 Harvie
2008/0091158 A1 4/2008 Yang
2008/0114327 A1 5/2008 Barge
2008/0140033 A1 6/2008 Burgess et al.
2008/0167634 A1 7/2008 Kouta et al.
2008/0183157 A1 7/2008 Walters
2008/0215031 A1 9/2008 Belfort et al.
2008/0234642 A1 9/2008 Patterson et al.
2008/0269703 A1 10/2008 Collins et al.
2008/0281282 A1 11/2008 Finger et al.
2008/0287894 A1 11/2008 Van Den Heuvel et al.
2008/0312550 A1 12/2008 Nishtala et al.
2009/0025717 A1 1/2009 Pinel
2009/0048570 A1 2/2009 Jensen
2009/0056003 A1 3/2009 Ivie et al.
2009/0069761 A1 3/2009 Vogel
2009/0069765 A1 3/2009 Wortham
2009/0120179 A1 5/2009 Nylander et al.
2009/0192482 A1 7/2009 Dodge et al.
2009/0226541 A1 9/2009 Scholz et al.
2009/0234312 A1 9/2009 Otoole et al.
2009/0251510 A1 10/2009 Noro et al.
2009/0254040 A1 10/2009 Bierman et al.
2009/0259206 A1 10/2009 Kai et al.
2009/0264840 A1 10/2009 Mrginio
2009/0270822 A1 10/2009 Medeiros
2009/0281510 A1 11/2009 Fisher
2009/0283982 A1 11/2009 Thomas
2009/0306610 A1 12/2009 Van Den Heuvel et al.
2010/0004612 A1 1/2010 Thevenin
2010/0030189 A1 2/2010 Fleming
2010/0031429 A1 2/2010 Kim et al.
2010/0032789 A1 2/2010 Schoen et al.
2010/0058660 A1 3/2010 Williams
2010/0121289 A1 5/2010 Parks et al.
2010/0158168 A1 6/2010 Murthy et al.
2010/0160882 A1 6/2010 Lowe
2010/0174250 A1 7/2010 Hu et al.
2010/0179493 A1 7/2010 Heagle et al.
2010/0185168 A1 7/2010 Graauw et al.
2010/0198172 A1 8/2010 Wada et al.
2010/0211032 A1 8/2010 Tsai et al.
2010/0234820 A1 9/2010 Tsai et al.
2010/0241104 A1 9/2010 Gilbert
2010/0263113 A1 10/2010 Shelton et al.
2010/0310845 A1 12/2010 Bond et al.
2011/0028920 A1 2/2011 Johannison
2011/0028922 A1 2/2011 Kay et al.
2011/0034889 A1 2/2011 Smith
2011/0036837 A1 2/2011 Shang
2011/0040267 A1 2/2011 Wada et al.
2011/0040271 A1 2/2011 Rogers et al.
2011/0054426 A1 3/2011 Stewart et al.
2011/0060299 A1 3/2011 Wada et al.
2011/0060300 A1 3/2011 Weig et al.
2011/0077495 A1 3/2011 Gilbert
2011/0077606 A1 3/2011 Wilcox et al.
2011/0087337 A1 4/2011 Forsell
2011/0137273 A1 6/2011 Muellejans et al.
2011/0145993 A1 6/2011 Rader et al.
2011/0152802 A1 6/2011 Dicamillo et al.
2011/0164147 A1 7/2011 Takahashi et al.
2011/0172620 A1 7/2011 Khambatta
2011/0172625 A1 7/2011 Wada et al.
2011/0198904 A1 8/2011 Thomas et al.
2011/0202024 A1 8/2011 Cozzens
2011/0238023 A1 9/2011 Slayton
2011/0240648 A1 10/2011 Tucker
2011/0251572 A1 10/2011 Nishtala et al.
2011/0265889 A1 11/2011 Tanaka et al.
2011/0276020 A1 11/2011 Mitsui
2012/0029452 A1 2/2012 Roedsten
2012/0035577 A1 2/2012 Tomes et al.
2012/0041400 A1 2/2012 Christensen
2012/0059328 A1 3/2012 Dikeman et al.
2012/0066825 A1 3/2012 Birbara et al.
2012/0103347 A1* 5/2012 Wheaton ................ A61F 5/453
128/885
2012/0116336 A1 5/2012 Sharma et al.
2012/0137420 A1 6/2012 Gordon et al.
2012/0165768 A1 6/2012 Sekiyama et al.
2012/0165786 A1 6/2012 Chappa et al.
2012/0209216 A1 8/2012 Jensen et al.
2012/0209225 A1 8/2012 Hu et al.
2012/0210503 A1 8/2012 Anzivino et al.
2012/0233761 A1 9/2012 Huang
2012/0245541 A1 9/2012 Suzuki et al.
2012/0245542 A1 9/2012 Suzuki et al.
2012/0245547 A1 9/2012 Wilcox et al.
2012/0253303 A1 10/2012 Suzuki et al.
2012/0271259 A1 10/2012 Ulert
2012/0296305 A1 11/2012 Barraza Khaled et al.
2012/0316522 A1 12/2012 Carter et al.
2012/0330256 A1 12/2012 Wilcox et al.
2013/0006206 A1 1/2013 Wada et al.
2013/0019374 A1 1/2013 Schwartz
2013/0036544 A1 2/2013 Lee et al.
2013/0045651 A1 2/2013 Esteves et al.
2013/0046258 A1 2/2013 Chambers
2013/0053804 A1 2/2013 Soerensen et al.
2013/0096523 A1 4/2013 Chang et al.
2013/0110059 A1 5/2013 Kossow et al.
2013/0138064 A1 5/2013 Stroebech et al.
2013/0144240 A1 6/2013 Ellis
2013/0150813 A1 6/2013 Gordon et al.
2013/0158494 A1 6/2013 Ong et al.
2013/0165880 A1 6/2013 Amos et al.
2013/0218112 A1 8/2013 Thompson
2013/0245496 A1 9/2013 Wells et al.
2013/0245586 A1 9/2013 Jha
2013/0274711 A1 10/2013 O'Day
2013/0292537 A1 11/2013 Dirico
2013/0330501 A1 12/2013 Aizenberg et al.
2014/0005647 A1 1/2014 Shuffler et al.
2014/0031774 A1 1/2014 Bengtson
2014/0039432 A1 2/2014 Dunbar et al.
2014/0039440 A1 2/2014 Doescher
2014/0058347 A1 2/2014 Marquette
2014/0107599 A1 4/2014 Fink et al.
2014/0157499 A1 6/2014 Suzuki et al.
2014/0171889 A1 6/2014 Hopman et al.
2014/0182051 A1 7/2014 Tanimoto et al.
2014/0196189 A1 7/2014 Lee et al.
2014/0257231 A1 9/2014 Wang et al.
2014/0276501 A1 9/2014 Cisko
2014/0303582 A1 10/2014 Wright et al.
2014/0316381 A1 10/2014 Reglin
2014/0325746 A1 11/2014 Block
2014/0348139 A1 11/2014 Gomez Martinez
2014/0352050 A1 12/2014 Yao et al.
2014/0371628 A1 12/2014 Desai
2015/0045757 A1 2/2015 Lee et al.

(56) References Cited

U.S. PATENT DOCUMENTS

2015/0047114 A1 2/2015 Ramirez
2015/0048089 A1 2/2015 Robertson
2015/0135423 A1 5/2015 Sharpe et al.
2015/0157300 A1 6/2015 Ealovega et al.
2015/0209188 A1 7/2015 Scheremet et al.
2015/0209194 A1 7/2015 Heyman
2015/0267862 A1 9/2015 Mishler
2015/0290421 A1 10/2015 Glickman et al.
2015/0290425 A1 10/2015 Macy et al.
2015/0320583 A1 11/2015 Harvie
2015/0329255 A1 11/2015 Rzepecki
2015/0342799 A1 12/2015 Michiels et al.
2015/0359660 A1 12/2015 Harvie
2015/0359996 A1 12/2015 Arora et al.
2015/0366699 A1 12/2015 Nelson
2016/0008193 A1 1/2016 Schulke
2016/0029998 A1 2/2016 Brister et al.
2016/0030228 A1 2/2016 Jones
2016/0038356 A1 2/2016 Yao et al.
2016/0051395 A1 2/2016 Ugarte M.D.
2016/0058322 A1 3/2016 Brister et al.
2016/0060001 A1 3/2016 Wada et al.
2016/0100976 A1 4/2016 Conway et al.
2016/0106604 A1 4/2016 Timm
2016/0113809 A1 4/2016 Kim
2016/0135792 A1 5/2016 Cai
2016/0136338 A1 5/2016 Lee et al.
2016/0183689 A1 6/2016 Miner
2016/0256022 A1 9/2016 Le
2016/0270982 A1 9/2016 Raycheck et al.
2016/0278662 A1 9/2016 Brister et al.
2016/0327553 A1 11/2016 Edwards et al.
2016/0357400 A1 12/2016 Penha et al.
2016/0366699 A1 12/2016 Zhang et al.
2016/0367226 A1 12/2016 Newton et al.
2016/0367411 A1 12/2016 Justiz et al.
2016/0367726 A1 12/2016 Gratzer
2016/0374848 A1 12/2016 Sanchez et al.
2017/0007438 A1 1/2017 Harvie
2017/0014560 A1 1/2017 Minskoff et al.
2017/0042724 A1 2/2017 Ugarte
2017/0042748 A1 2/2017 Griffin
2017/0100276 A1 4/2017 Joh
2017/0107312 A1 4/2017 Hinayama et al.
2017/0128638 A1 5/2017 Giezendanner et al.
2017/0136209 A1 5/2017 Burnett et al.
2017/0143534 A1 5/2017 Sanchez
2017/0165100 A1 6/2017 Jackson et al.
2017/0165405 A1 6/2017 Muser et al.
2017/0189225 A1 7/2017 Voorhees et al.
2017/0202692 A1 7/2017 Laniado
2017/0216081 A1 8/2017 Accosta
2017/0238911 A1 8/2017 Duval
2017/0246026 A1 8/2017 Laniado
2017/0252014 A1 9/2017 Siller Gonzalez et al.
2017/0252202 A9 9/2017 Sanchez et al.
2017/0266031 A1 9/2017 Sanchez et al.
2017/0266658 A1 9/2017 Bruno et al.
2017/0281399 A1 10/2017 Vanmiddendorp et al.
2017/0281419 A1 10/2017 Pintado
2017/0312116 A1 11/2017 Laniado
2017/0325788 A1 11/2017 Ealovega et al.
2017/0333244 A1 11/2017 Laniado
2017/0348139 A1 12/2017 Newton et al.
2017/0354532 A1 12/2017 Holt
2017/0354551 A1 12/2017 Gawley et al.
2017/0367873 A1 12/2017 Grannum
2018/0002075 A1 1/2018 Lee
2018/0008451 A1 1/2018 Stroebech
2018/0008804 A1 1/2018 Laniado
2018/0021218 A1 1/2018 Brosch et al.
2018/0028349 A1* 2/2018 Newton .................. A61M 1/88
2018/0037384 A1 2/2018 Archeny et al.
2018/0049910 A1 2/2018 Newton
2018/0064572 A1 3/2018 Wiltshire
2018/0104131 A1 4/2018 Killian
2018/0127187 A1 5/2018 Sewell
2018/0149635 A1 5/2018 Abir
2018/0169281 A1 6/2018 Russell et al.
2018/0193215 A1 7/2018 Davies et al.
2018/0200101 A1 7/2018 Su
2018/0214297 A1 8/2018 Hughett et al.
2018/0221216 A1 8/2018 Benz et al.
2018/0228642 A1 8/2018 Davis et al.
2018/0229014 A1 8/2018 Guirguis et al.
2018/0256384 A1 9/2018 Kasirye
2018/0271694 A1 9/2018 Fernandez et al.
2018/0280236 A1 10/2018 Ludin et al.
2018/0317892 A1 11/2018 Catlin
2018/0325748 A1 11/2018 Sharma et al.
2019/0001029 A1 1/2019 Davie et al.
2019/0001030 A1 1/2019 Braga et al.
2019/0021899 A1 1/2019 Vlet
2019/0038451 A1 2/2019 Harvie
2019/0046102 A1 2/2019 Kushnir et al.
2019/0059938 A1 2/2019 Holsten
2019/0091059 A1 3/2019 Gabriel
2019/0100362 A1 4/2019 Meyers et al.
2019/0133126 A1 5/2019 Modak et al.
2019/0133814 A1 5/2019 Tammen et al.
2019/0142624 A1 5/2019 Sanchez et al.
2019/0224036 A1 7/2019 Sanchez et al.
2019/0226189 A1 7/2019 Braxton
2019/0240079 A1 8/2019 Tuli
2019/0247222 A1 8/2019 Ecklund et al.
2019/0247223 A1 8/2019 Brun et al.
2019/0247623 A1 8/2019 Helm et al.
2019/0282391 A1 9/2019 Johannes et al.
2019/0314189 A1 10/2019 Acosta
2019/0314190 A1 10/2019 Sanchez et al.
2019/0321587 A1 10/2019 Mcmenamin et al.
2019/0344934 A1 11/2019 Faerber et al.
2019/0365303 A1 12/2019 Bullington et al.
2019/0365307 A1 12/2019 Laing et al.
2019/0365561 A1 12/2019 Newton et al.
2019/0374373 A1 12/2019 Joh
2020/0008985 A1 1/2020 Nguyen et al.
2020/0016012 A1 1/2020 Dutkiewicz
2020/0030595 A1 1/2020 Boukidjian et al.
2020/0040561 A1 2/2020 Sugawara
2020/0046544 A1 2/2020 Godinez et al.
2020/0055638 A1 2/2020 Lau et al.
2020/0070392 A1 3/2020 Huber et al.
2020/0085609 A1 3/2020 Schelch et al.
2020/0085610 A1 3/2020 Cohn et al.
2020/0086090 A1 3/2020 Von Weymarn-Schärli et al.
2020/0107518 A1 4/2020 Hiroshima et al.
2020/0129322 A1 4/2020 Leuckel
2020/0171217 A9 6/2020 Braga et al.
2020/0179177 A1 6/2020 Erdem et al.
2020/0187918 A1 6/2020 Wiygul
2020/0206015 A1 7/2020 Langer
2020/0206039 A1 7/2020 Mclain
2020/0214910 A1 7/2020 Varona et al.
2020/0216898 A1 7/2020 Hubbell
2020/0216989 A1 7/2020 Kinugasa et al.
2020/0229964 A1 7/2020 Staali et al.
2020/0231343 A1 7/2020 Freedman et al.
2020/0232841 A1 7/2020 Satish et al.
2020/0246172 A1 8/2020 Ho
2020/0246203 A1 8/2020 Tulk et al.
2020/0255189 A1 8/2020 Liu
2020/0261280 A1 8/2020 Heyman
2020/0276046 A1 9/2020 Staali et al.
2020/0306075 A1 10/2020 Newton et al.
2020/0315837 A1 10/2020 Radl et al.
2020/0315838 A1 10/2020 Eckert
2020/0315872 A1 10/2020 Viens et al.
2020/0315874 A1 10/2020 Viens et al.
2020/0331672 A1 10/2020 Bertram et al.
2020/0345332 A1 11/2020 Duval
2020/0353135 A1 11/2020 Gregory et al.
2020/0367677 A1 11/2020 Silsby et al.
2020/0369444 A1 11/2020 Silsby et al.

(56) References Cited

U.S. PATENT DOCUMENTS

2020/0375781 A1 12/2020 Staali et al.
2020/0375810 A1 12/2020 Carlin et al.
2020/0384242 A1 12/2020 Havard et al.
2020/0385179 A1 12/2020 Mccourt
2020/0390591 A1 12/2020 Glithero et al.
2020/0390592 A1 12/2020 Merrill
2020/0398024 A1 12/2020 Fletter et al.
2020/0405521 A1 12/2020 Glasroe
2021/0008771 A1 1/2021 Huber et al.
2021/0009323 A1 1/2021 Markarian et al.
2021/0020072 A1 1/2021 Moehring et al.
2021/0023279 A1 1/2021 Radl et al.
2021/0059853 A1 3/2021 Davis et al.
2021/0061523 A1 3/2021 Bytheway
2021/0069005 A1 3/2021 Sanchez et al.
2021/0069008 A1 3/2021 Blabas et al.
2021/0069009 A1 3/2021 Im
2021/0069030 A1 3/2021 Nishikawa et al.
2021/0077993 A1 3/2021 Nazareth et al.
2021/0113749 A1 4/2021 Radl et al.
2021/0121318 A1 4/2021 Pinlac
2021/0137724 A1 5/2021 Ecklund et al.
2021/0138190 A1 5/2021 Erbey et al.
2021/0154055 A1 5/2021 Villarreal
2021/0170079 A1 6/2021 Radl et al.
2021/0178390 A1 6/2021 Oueslati et al.
2021/0186742 A1 6/2021 Newton et al.
2021/0186744 A1 6/2021 Spector
2021/0211568 A1 7/2021 Zhou et al.
2021/0212865 A1 7/2021 Wallajapet et al.
2021/0220162 A1 7/2021 Jamison
2021/0220163 A1 7/2021 Mayrand
2021/0228400 A1 7/2021 Glithero
2021/0228401 A1 7/2021 Becker et al.
2021/0228795 A1 7/2021 Hughett et al.
2021/0229877 A1 7/2021 Ragias et al.
2021/0236323 A1 8/2021 Austermann et al.
2021/0236324 A1 8/2021 Sweeney
2021/0251814 A1 8/2021 Jönegren et al.
2021/0267787 A1 9/2021 Nazemi
2021/0275343 A1 9/2021 Sanchez et al.
2021/0275344 A1 9/2021 Wing
2021/0290454 A1 9/2021 Yamada
2021/0290464 A1 9/2021 Furuta
2021/0315726 A1 10/2021 Lin
2021/0315727 A1 10/2021 Jiang
2021/0353449 A1 11/2021 Sharma et al.
2021/0353450 A1 11/2021 Sharma et al.
2021/0361469 A1 11/2021 Liu et al.
2021/0369495 A1 12/2021 Cheng et al.
2021/0386925 A1 12/2021 Hartwell et al.
2021/0393433 A1 12/2021 Godinez et al.
2022/0023091 A1 1/2022 Ecklund et al.
2022/0026546 A1 1/2022 Aono et al.
2022/0031290 A1 2/2022 Weed
2022/0031523 A1 2/2022 Pierpoint
2022/0039995 A1 2/2022 Johannes et al.
2022/0047410 A1 2/2022 Walthall
2022/0062025 A1 3/2022 Shields et al.
2022/0062027 A1 3/2022 Mitchell et al.
2022/0062028 A1 3/2022 Mitchell et al.
2022/0062029 A1 3/2022 Johannes et al.
2022/0066825 A1 3/2022 Saraf et al.
2022/0071811 A1 3/2022 Cheng et al.
2022/0071826 A1 3/2022 Kulkarni et al.
2022/0104965 A1 4/2022 Vaninetti et al.
2022/0104976 A1 4/2022 Hoeger et al.
2022/0104981 A1 4/2022 Jones
2022/0117773 A1 4/2022 Davis et al.
2022/0117774 A1 4/2022 Meyer et al.
2022/0117775 A1 4/2022 Jones et al.
2022/0118165 A1 4/2022 Knapp et al.
2022/0133524 A1 5/2022 Davis
2022/0151817 A1 5/2022 Mann
2022/0160949 A1 5/2022 Simiele et al.
2022/0168159 A1 6/2022 Triado et al.
2022/0193312 A1 6/2022 Lee et al.
2022/0211536 A1 7/2022 Johannes et al.
2022/0218510 A1 7/2022 Metzger et al.
2022/0229053 A1 7/2022 Levin et al.
2022/0241106 A1 8/2022 Johannes et al.
2022/0247407 A1 8/2022 Yamamoto et al.
2022/0248836 A1 8/2022 Cagle et al.
2022/0257407 A1 8/2022 Johannes et al.
2022/0265460 A1 8/2022 Coker
2022/0265462 A1 8/2022 Alder et al.
2022/0270711 A1 8/2022 Feala et al.
2022/0273482 A1 9/2022 Johannes et al.
2022/0280357 A1 9/2022 Jagannathan et al.
2022/0280710 A1 9/2022 Agrawal et al.
2022/0287689 A1 9/2022 Johannes
2022/0287867 A1 9/2022 Jones et al.
2022/0287868 A1 9/2022 Garvey et al.
2022/0296408 A1 9/2022 Evans et al.
2022/0305191 A1 9/2022 Joseph et al.
2022/0313222 A1 10/2022 Austermann et al.
2022/0313474 A1 10/2022 Kriscovich et al.
2022/0331170 A1 10/2022 Erdem et al.
2022/0339023 A1 10/2022 Davis et al.
2022/0339024 A1 10/2022 Johannes et al.
2022/0354685 A1 11/2022 Davis et al.
2022/0362049 A1 11/2022 Austermann et al.
2022/0370231 A1 11/2022 Wang et al.
2022/0370234 A1 11/2022 Hughett et al.
2022/0370235 A1 11/2022 Johannes et al.
2022/0370237 A1 11/2022 Parmar et al.
2022/0387001 A1 12/2022 Askenazi et al.
2022/0387693 A1 12/2022 Bannwart et al.
2022/0395390 A1 12/2022 Brooks
2022/0395391 A1 12/2022 Saunders et al.
2022/0401252 A1 12/2022 Warren
2022/0409419 A1 12/2022 Garvey et al.
2022/0409422 A1 12/2022 Schneider et al.
2023/0018845 A1 1/2023 Lee
2023/0020563 A1 1/2023 Sharma et al.
2023/0031640 A1 2/2023 Hughett et al.
2023/0037159 A1 2/2023 Brennan et al.
2023/0049924 A1 2/2023 Johannes et al.
2023/0052238 A1 2/2023 Oluwasogo
2023/0062994 A1 3/2023 Ecklund et al.
2023/0070347 A1 3/2023 Watson et al.
2023/0073708 A1 3/2023 Xu et al.
2023/0089032 A1 3/2023 Hughett et al.
2023/0091118 A1 3/2023 Watson
2023/0099821 A1 3/2023 Radl et al.
2023/0099991 A1 3/2023 Bianchi et al.
2023/0105001 A1 4/2023 Whittome et al.
2023/0110577 A1 4/2023 Choi
2023/0138269 A1 5/2023 Abdelal et al.
2023/0145365 A1 5/2023 Martin et al.
2023/0155253 A1 5/2023 Mn et al.
2023/0190511 A1 6/2023 Sharma et al.
2023/0210504 A1 7/2023 Kuroda et al.
2023/0210685 A1 7/2023 Fallows et al.
2023/0218426 A1 7/2023 Hughett
2023/0240884 A1 8/2023 Davis et al.
2023/0248562 A1 8/2023 Sanchez et al.
2023/0248564 A1 8/2023 Mann et al.
2023/0255812 A1 8/2023 Sanchez et al.
2023/0255813 A1 8/2023 Sanchez et al.
2023/0255815 A1 8/2023 Newton
2023/0263650 A1 8/2023 Sanchez et al.
2023/0263655 A1 8/2023 Johannes et al.
2023/0277360 A1 9/2023 Lambert et al.
2023/0277362 A1 9/2023 Davis et al.
2023/0285178 A1 9/2023 Sanchez et al.
2023/0293339 A1 9/2023 James
2023/0301846 A1 9/2023 Greenwood
2023/0355423 A1 11/2023 Stevenson et al.
2023/0389900 A1 12/2023 Xie et al.
2023/0404791 A1 12/2023 Ecklund et al.
2024/0008444 A1 1/2024 Su et al.
2024/0009023 A1 1/2024 Johannes et al.
2024/0024170 A1 1/2024 Scott

(56) References Cited

U.S. PATENT DOCUMENTS

| | | | |
|---|---|---|---|
| 2024/0033148 | A1 | 2/2024 | Gordon et al. |
| 2024/0041638 | A1 | 2/2024 | Johannes et al. |
| 2024/0058157 | A1 | 2/2024 | Davis |
| 2024/0058160 | A1 | 2/2024 | Young Joyner et al. |
| 2024/0058161 | A1 | 2/2024 | Ulreich et al. |
| 2024/0058520 | A1 | 2/2024 | Yin et al. |
| 2024/0065881 | A1 | 2/2024 | Kuroda et al. |
| 2024/0082044 | A1 | 3/2024 | Nguyen et al. |
| 2024/0099874 | A1 | 3/2024 | Sanchez et al. |
| 2024/0108268 | A1 | 4/2024 | Woodard et al. |
| 2024/0110318 | A1 | 4/2024 | Bendt et al. |
| 2024/0122773 | A1 | 4/2024 | Nguyen et al. |
| 2024/0123134 | A1 | 4/2024 | Kharkar et al. |
| 2024/0130885 | A1 | 4/2024 | Young Joyner et al. |
| 2024/0148539 | A1 | 5/2024 | Austermann et al. |
| 2024/0156633 | A1 | 5/2024 | Fallows et al. |
| 2024/0164935 | A1 | 5/2024 | Newton |
| 2024/0252343 | A1 | 8/2024 | Voda |
| 2024/0261131 | A1 | 8/2024 | Garvey et al. |
| 2024/0268986 | A1 | 8/2024 | Barnes et al. |
| 2024/0268989 | A1 | 8/2024 | Martin et al. |
| 2024/0268991 | A1 | 8/2024 | Davis |
| 2024/0269027 | A1 | 8/2024 | Tourchak et al. |
| 2024/0285425 | A1 | 8/2024 | Donohoe et al. |
| 2024/0325190 | A1 | 10/2024 | Minchew et al. |
| 2024/0358539 | A1 | 10/2024 | Gallup |
| 2024/0358542 | A1 | 10/2024 | Richardson et al. |
| 2024/0374414 | A1 | 11/2024 | Richardson et al. |
| 2025/0009552 | A1 | 1/2025 | Blabas et al. |
| 2025/0073055 | A1 | 3/2025 | Ecklund et al. |
| 2025/0107920 | A1 | 4/2025 | Fallows et al. |
| 2025/0107921 | A1 | 4/2025 | Sanchez et al. |

FOREIGN PATENT DOCUMENTS

| | | | |
|---|---|---|---|
| AU | 2022349367 | | 4/2024 |
| CA | 2165286 | C | 9/1999 |
| CA | 2335223 | | 1/2000 |
| CA | 2354132 | A1 | 6/2000 |
| CA | 2359091 | C | 9/2003 |
| CA | 2488867 | C | 8/2007 |
| CA | 3031934 | | 2/2018 |
| CA | 3050918 | A1 | 8/2018 |
| CA | 3098571 | A1 | 11/2019 |
| CA | 3144181 | | 1/2021 |
| CA | 3188651 | | 7/2023 |
| CN | 2269203 | Y | 12/1997 |
| CN | 1332620 | A | 1/2002 |
| CN | 1434693 | A | 8/2003 |
| CN | 1533755 | A | 10/2004 |
| CN | 1579348 | | 2/2005 |
| CN | 1602825 | A | 4/2005 |
| CN | 1638708 | | 7/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 202950810 | U | 5/2013 |
| CN | 103533968 | A | 1/2014 |
| CN | 103717180 | A | 4/2014 |
| CN | 204562697 | U | 8/2015 |
| CN | 105411783 | A | 3/2016 |
| CN | 105451693 | A | 3/2016 |
| CN | 105534632 | A | 5/2016 |
| CN | 106132360 | A | 11/2016 |
| CN | 205849719 | U | 1/2017 |
| CN | 205924282 | U | 2/2017 |
| CN | 106726089 | A | 5/2017 |
| CN | 107847384 | A | 3/2018 |
| CN | 107920912 | A | 4/2018 |
| CN | 108420590 | A | 8/2018 |
| CN | 209285902 | U | 8/2019 |
| CN | 110381883 | A | 10/2019 |
| CN | 211198839 | U | 8/2020 |
| CN | 111991136 | A | 11/2020 |
| CN | 112022488 | A | 12/2020 |
| CN | 212234893 | U | 12/2020 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 202005013173 | | 6/2006 |
| DE | 102005037762 | B3 | 9/2006 |
| DE | 102011103783 | A1 | 12/2012 |
| DE | 102012112818 | A1 | 6/2014 |
| DE | 202015104597 | U1 | 7/2016 |
| DE | 102018118570 | | 2/2020 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | | 5/1992 |
| EP | 0610638 | A1 | 8/1994 |
| EP | 0613355 | A1 | 9/1994 |
| EP | 0711536 | | 5/1996 |
| EP | 0613355 | B1 | 1/1997 |
| EP | 0680296 | | 5/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2470251 | | 12/2014 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3777801 | | 2/2021 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3749230 | | 3/2023 |
| EP | 3569205 | B1 | 6/2023 |
| EP | 4192402 | | 6/2023 |

(56) References Cited

FOREIGN PATENT DOCUMENTS

| | | | |
|---|---|---|---|
| EP | 4218702 | | 8/2023 |
| EP | 3624742 | | 1/2024 |
| EP | 4382082 | A2 | 6/2024 |
| EP | 4445881 | A2 | 10/2024 |
| EP | 4464288 | A2 | 11/2024 |
| EP | 4215134 | | 1/2025 |
| EP | 4494611 | | 1/2025 |
| EP | 4527361 | | 3/2025 |
| FR | 2826704 | | 1/2003 |
| GB | 871820 | A | 7/1961 |
| GB | 0873045 | | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2415386 | | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H08117271 | A | 5/1996 |
| JP | H08510924 | A | 11/1996 |
| JP | 2686634 | B2 | 12/1997 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | | 1/2002 |
| JP | 2002102285 | | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | | 8/2003 |
| JP | 2003528691 | A | 9/2003 |
| JP | 2004057578 | A | 2/2004 |
| JP | 2004130056 | A | 4/2004 |
| JP | 2004267400 | | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136491 | | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | | 8/2011 |
| JP | 2011202664 | | 10/2011 |
| JP | 2011218130 | A | 11/2011 |
| JP | 2011224070 | A | 11/2011 |
| JP | 3175719 | U | 4/2012 |
| JP | 2012522014 | | 9/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 3208707 | U | 2/2017 |
| JP | 3209321 | U | 3/2017 |
| JP | 2017070400 | | 4/2017 |
| JP | 2017512603 | A | 5/2017 |
| JP | 2017127596 | | 7/2017 |
| JP | 2017201272 | A | 11/2017 |
| JP | 2019010375 | | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020510464 | | 4/2020 |
| JP | 2020520775 | A | 7/2020 |
| JP | 2020124425 | | 8/2020 |
| JP | 2021007472 | A | 1/2021 |
| JP | 2021041145 | | 3/2021 |
| JP | 2021074491 | | 5/2021 |
| JP | 2021120686 | A | 8/2021 |
| JP | 2021520952 | | 8/2021 |
| JP | 2021522009 | A | 8/2021 |
| JP | 2021522013 | A | 8/2021 |
| JP | 2021522019 | A | 8/2021 |
| JP | 7129493 | B2 | 8/2022 |
| JP | 2022554252 | A | 12/2022 |
| JP | 2023532132 | A | 7/2023 |
| KR | 200290061 | Y1 | 9/2002 |

(56) References Cited

FOREIGN PATENT DOCUMENTS

| | | | |
|---|---|---|---|
| KR | 20030047451 | A | 6/2003 |
| KR | 20080005516 | A | 1/2008 |
| KR | 20090072069 | A | 7/2009 |
| KR | 20090104426 | A | 10/2009 |
| KR | 20090110359 | A | 10/2009 |
| KR | 20120005922 | A | 1/2012 |
| KR | 20140039485 | A | 4/2014 |
| KR | 101432639 | B1 | 8/2014 |
| KR | 20180106659 | A | 10/2018 |
| KR | 20180108774 | A | 10/2018 |
| KR | 20230034343 | A | 3/2023 |
| PT | 2068717 | E | 6/2013 |
| SE | 505542 | C2 | 9/1997 |
| TW | 408207 | B | 10/2000 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |
| WO | 9416914 | A1 | 8/1994 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03015671 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005051252 | A1 | 6/2005 |
| WO | 2005060558 | A2 | 7/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017100511 | A1 | 6/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |

(56) References Cited

FOREIGN PATENT DOCUMENTS

WO 2019065541 A1 4/2019
WO 2019096845 A1 5/2019
WO 2019150385 A1 8/2019
WO 2019161094 A1 8/2019
WO 2019188566 A1 10/2019
WO 2019190593 A1 10/2019
WO 2019212949 A1 11/2019
WO 2019212950 A1 11/2019
WO 2019212951 A1 11/2019
WO 2019212952 A1 11/2019
WO 2019212954 A1 11/2019
WO 2019212955 A1 11/2019
WO 2019212956 A1 11/2019
WO 2019214787 A1 11/2019
WO 2019214788 A1 11/2019
WO 2019226826 A1 11/2019
WO 2019239433 A1 12/2019
WO 2020000994 A1 1/2020
WO 2020020618 A1 1/2020
WO 2020033752 A1 2/2020
WO 2020038822 A1 2/2020
WO 2020088409 A1 5/2020
WO 2020049394 A3 6/2020
WO 2020120657 A1 6/2020
WO 2020152575 A1 7/2020
WO 2020182923 A1 9/2020
WO 2020204967 A1 10/2020
WO 2020205939 A1 10/2020
WO 2020209898 A1 10/2020
WO 2020242790 A1 12/2020
WO 2020251893 A1 12/2020
WO 2020256865 A1 12/2020
WO 2021007144 A1 1/2021
WO 2021007345 A1 1/2021
WO 2021010844 A1 1/2021
WO 2021016026 A1 1/2021
WO 2021016056 A1 1/2021
WO 2021016300 A1 1/2021
WO 2021025919 A1 2/2021
WO 2021034886 A1 2/2021
WO 2021041123 A1 3/2021
WO 2021046501 A1 3/2021
WO 2021086868 A1 5/2021
WO 2021094352 A1 5/2021
WO 2021094639 A1 5/2021
WO 2021097067 A1 5/2021
WO 2021102296 A1 5/2021
WO 2021107025 A1 6/2021
WO 2021138411 A1 7/2021
WO 2021138414 A1 7/2021
WO 2021154686 A1 8/2021
WO 2021155206 A1 8/2021
WO 2021170075 A1 9/2021
WO 2021173436 A1 9/2021
WO 2021188817 A1 9/2021
WO 2021195384 A1 9/2021
WO 2021205995 A1 10/2021
WO 2021207621 A1 10/2021
WO 2021211568 A1 10/2021
WO 2021211801 A1 10/2021
WO 2021211914 A1 10/2021
WO 2021216419 A1 10/2021
WO 2021216422 A1 10/2021
WO 2021231532 A1 11/2021
WO 2021247523 A1 12/2021
WO 2021257202 A1 12/2021
WO 2022006256 A1 1/2022
WO 2022029662 A1 2/2022
WO 2022031943 A1 2/2022
WO 2022035745 A1 2/2022
WO 2022051220 A1 3/2022
WO 2022051360 A1 3/2022
WO 2022054613 A1 3/2022
WO 2022066704 A1 3/2022
WO 2022067392 A1 4/2022
WO 2022069950 A1 4/2022
WO 2022071429 A1 4/2022
WO 2022076322 A1 4/2022
WO 2022076427 A2 4/2022
WO 2022086898 A1 4/2022
WO 2022090199 A1 5/2022
WO 2022098536 A1 5/2022
WO 2022099087 A1 5/2022
WO 2022101999 A1 5/2022
WO 2022115692 A1 6/2022
WO 2022125685 A1 6/2022
WO 2022140545 A1 6/2022
WO 2022145231 A1 7/2022
WO 2022150290 A1 7/2022
WO 2022150360 A1 7/2022
WO 2022150463 A1 7/2022
WO 2022159392 A1 7/2022
WO 2022170182 A1 8/2022
WO 2022173803 A1 8/2022
WO 2022182385 A1 9/2022
WO 2022187152 A1 9/2022
WO 2022192188 A1 9/2022
WO 2022192347 A1 9/2022
WO 2022204000 A1 9/2022
WO 2022216507 A1 10/2022
WO 2022216776 A1 10/2022
WO 2022222030 A1 10/2022
WO 2022251184 A1 12/2022
WO 2022251425 A1 12/2022
WO 2022271783 A1 12/2022
WO 2023286058 A1 1/2023
WO 2023014639 A1 2/2023
WO 2023014641 A1 2/2023
WO 2023018475 A2 2/2023
WO 2023018656 A1 2/2023
WO 2023018657 A1 2/2023
WO 2023023777 A1 3/2023
WO 2023034139 A1 3/2023
WO 2023034453 A1 3/2023
WO 2023038945 A1 3/2023
WO 2023038950 A1 3/2023
WO 2023049109 A1 3/2023
WO 2023049156 A1 3/2023
WO 2023049175 A1 3/2023
WO 2023086394 A1 5/2023
WO 2023149884 A1 8/2023
WO 2023149902 A1 8/2023
WO 2023149903 A1 8/2023
WO 2023154390 A1 8/2023
WO 2023163725 A1 8/2023
WO 2023191764 A1 10/2023
WO 2023244238 A1 12/2023
WO 2024043871 A1 2/2024
WO 2024058788 A1 3/2024
WO 2024253655 A1 12/2024
WO 2025034959 A1 2/2025
WO 2025038087 A1 2/2025
WO 2025038088 A1 2/2025
WO 2025048789 A1 3/2025
WO 2025071622 A1 4/2025
WO 2025179267 A1 8/2025

OTHER PUBLICATIONS

"Dictionary.com, ABUT Definition & Meaning, 2024, Dictionary.com, https://www.dictionary.com/browse/abut" (Year: 2024).*

Dictionary.com, Definition of PROXIMATE, 2025 (Year: 2025).*

Advisory Action for U.S. Appl. No. 16/245,726 mailed Apr. 19, 2023.

Advisory Action for U.S. Appl. No. 16/369,676 mailed Mar. 24, 2023.

Advisory Action for U.S. Appl. No. 16/433,773 mailed Dec. 29, 2023.

Advisory Action for U.S. Appl. No. 16/433,773 mailed Feb. 15, 2023.

Advisory Action for U.S. Appl. No. 16/449,039 mailed Jan. 25, 2024.

(56) References Cited

OTHER PUBLICATIONS

Advisory Action for U.S. Appl. No. 16/452,258 mailed Oct. 26, 2022.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/450,864 mailed on Mar. 21, 2024.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/478,180 mailed May 31, 2023.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/IB2021/057173 mailed Nov. 5, 2021.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015781 mailed May 6, 2022.
International Search Report and Written Opinion from International Application No. PCT/US2022/018159 mailed Dec. 12, 2022.
International Search Report and Written Opinion from International Application No. PCT/US2022/022111 mailed Oct. 26, 2022.

(56) References Cited

OTHER PUBLICATIONS

International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
Issue Notification for U.S. Appl. No. 16/245,726 mailed Oct. 18, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Apr. 11, 2023.
Non-Final Office Action for U.S. Appl. No. 16/433,773 mailed Feb. 26, 2024.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/904,868 mailed Mar. 12, 2024.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,256 mailed Feb. 13, 2024.
Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,345 mailed Jan. 17, 2024.
Non-Final Office Action for U.S. Appl. No. 17/451,354 mailed May 3, 2023.
Non-Final Office Action for U.S. Appl. No. 17/453,260 mailed Mar. 14, 2023.

(56) References Cited

OTHER PUBLICATIONS

Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/597,673 mailed Mar. 20, 2024.
Non-Final Office Action for U.S. Appl. No. 17/645,821 mailed Oct. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/653,920 mailed Mar. 15, 2024.
Non-Final Office Action for U.S. Appl. No. 17/655,464 mailed Mar. 14, 2023.
Non-Final Office Action for U.S. Appl. No. 17/655,464 mailed Mar. 26, 2024.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/164,800 mailed Mar. 22, 2024.
Non-Final Office Action for U.S. Appl. No. 18/198,464 mailed Dec. 7, 2023.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/899,956 mailed Dec. 1, 2022.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/326,980 mailed Jan. 29, 2024.
Notice of Allowance for U.S. Appl. No. 17/453,560 mailed Jan. 31, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/657,474 mailed Mar. 5, 2024.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 17/667,097 mailed Mar. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 17/444,792, filed Aug. 10, 2021.
U.S. Appl. No. 17/451,719, filed Oct. 19, 2021.
U.S. Appl. No. 17/664,487, filed May 23, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/249,577, filed Oct. 19, 2021.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.

(56) References Cited

OTHER PUBLICATIONS

U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 63/150,640, filed Feb. 18, 2021.
U.S. Appl. No. 63/308,190, filed Feb. 9, 2022.
U.S. Appl. No. 63/561,893, filed Dec. 11, 2023.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, March/Apr. 1993, pp. 51-55.
MNAS,"A Solution for an Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article,"Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/452,145 mailed Mar. 25, 2022.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.

(56) References Cited

OTHER PUBLICATIONS

International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/012794 mailed May 3, 2022.
International Search Report and Written Opinion from International Application No. PCT/US2022015471 mailed May 16, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.

(56) References Cited

OTHER PUBLICATIONS

Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/899,956 mailed Apr. 19, 2022.
Notice of Allowance for U.S. Appl. No. 16/899,956 mailed Dec. 29, 2021.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/384,196, filed Dec. 19, 2016.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.

(56) References Cited

OTHER PUBLICATIONS

U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914 filed May 25, 222.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,977, filed Jan. 30, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.

(56) References Cited

OTHER PUBLICATIONS

U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
BOEHRINGER CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
Macaulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
Purewick , "Incontinence Relief for Women", Presentation, Sep. 23, 2015, 7 pages.
Pytlik , "Super Absorbent Polymers", University of Buffalo.
Sachtman , "New Relief for Pilots? It Depends", Wired, 2008, 2 pages.
Tsipenyuk , et al., "Use of biomimetic hexagonal surface texture in friction against lubricated skin", Journal of The Royal Society—Interface, 2014, pp. 1-6.

(56) References Cited

OTHER PUBLICATIONS

Advisory Action for U.S. Appl. No. 16/478,180 mailed Sep. 21, 2022.
Advisory Action for U.S. Appl. No. 16/904,868 mailed Jun. 15, 2022.
Final Office Action for U.S. Appl. No. 16/449,039 mailed Aug. 1, 2022.
Final Office Action for U.S. Appl. No. 16/452,258 mailed Jun. 14, 2022.
Final Office Action for U.S. Appl. No. 16/478,180 mailed Jun. 22, 2022.
International Search Report and Written Opinion from International Application No. PCT/US2021/039866 mailed Oct. 7, 2021.
International Search Report and Written Opinion from International Application No. PCT/US2021/055515 mailed Jan. 28, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/015492 mailed Apr. 26, 2022.
International Search Report and Written Opinion from International Application No. PCT/US2022/016942 mailed Jun. 8, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
Issue Notification for U.S. Appl. No. 17/088,272 mailed Jun. 15, 2022.
Issue Notification for U.S. Appl. No. 17/330,657 mailed Jun. 22, 2022.
Non-Final Office Action for U.S. Appl. No. 17/662,700 mailed Jul. 22, 2022.
Notice of Allowance for U.S. Appl. No. 16/899,956 mailed Aug. 10, 2022.
Notice of Allowance for U.S. Appl. No. 16/905,400 mailed Aug. 17, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 62/967,158, filed Jan. 26, 2020.
U.S. Appl. No. 62/991,754, filed Mar. 19, 2020.
U.S. Appl. No. 63/241,328, filed Sep. 7, 2021.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/446,256 mailed Nov. 19, 2024.
Advisory Action for U.S. Appl. No. 17/446,654 mailed Apr. 15, 2024.
Advisory Action for U.S. Appl. No. 17/451,345 mailed Jul. 3, 2024.
Advisory Action for U.S. Appl. No. 17/597,673 mailed Jan. 7, 2025.
Advisory Action for U.S. Appl. No. 17/645,821 mailed Jul. 2, 2024.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 17/808,354 mailed Jun. 12, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Jan. 8, 2025.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/451,345 mailed Feb. 6, 2025.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,673 mailed Oct. 22, 2024.
Final Office Action for U.S. Appl. No. 17/645,821 mailed Apr. 3, 2024.
Final Office Action for U.S. Appl. No. 17/653,137 mailed Aug. 7, 2024.
Final Office Action for U.S. Appl. No. 17/653,314 mailed Jan. 30, 2025.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 17/808,354 mailed Apr. 10, 2024.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/164,800 mailed Oct. 22, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/036238 mailed Jul. 22, 2024.

(56) References Cited

OTHER PUBLICATIONS

International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Issue Notification for U.S. Appl. No. 17/661,090 mailed Feb. 5, 2025.
Issue Notification for U.S. Appl. No. 17/662,700 mailed Oct. 23, 2024.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/198,464 mailed Nov. 20, 2024.
Issue Notification for U.S. Appl. No. 18/389,009 mailed Dec. 18, 2024.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 17/378,015 mailed Jul. 5, 2024.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,345 mailed Jul. 25, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/646,771 mailed Apr. 24, 2024.
Non-Final Office Action for U.S. Appl. No. 17/653,137 mailed Jan. 28, 2025.
Non-Final Office Action for U.S. Appl. No. 17/653,314 mailed Aug. 29, 2024.
Non-Final Office Action for U.S. Appl. No. 17/653,920 mailed Nov. 27, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/749,340 mailed Aug. 14, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/907,125 mailed Dec. 13, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/326,980 mailed Apr. 5, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/453,260 mailed Apr. 8, 2024.

(56) References Cited

OTHER PUBLICATIONS

Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/596,629 mailed Jan. 29, 2025.
Notice of Allowance for U.S. Appl. No. 17/646,771 mailed Dec. 17, 2024.
Notice of Allowance for U.S. Appl. No. 17/657,474 mailed May 2, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Apr. 17, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
U.S. Appl. No. 17/013,822, filed Sep. 7, 2020.
U.S. Appl. No. 18/662,216, filed May 13, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197 filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 63/181,709, filed Apr. 29, 2021.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"OBLONG", Cambridge Dictionary, https://dictionary.cambridge.org/dictionary/english/oblong, 2024, 1 page.
Britannica , "Polyolefin", Britannica Online Encyclopedia, T. Editors of Encyclopaedia, https://www.britannica.com/science/polyolefin, Jul. 26, 2012.
Martin , "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia article , "Decibel", https://web.archive.org/web/20200415121917/https://en.wikipedia/org/wiki/Decibel last accessed Mar. 11, 2024, 21 pages.
Wikipedia article , "Fiberglass", https://web.archive.org.web/20200309194847/https://en.wikipedia.org/wiki/Fiberglass last accessed Mar. 11, 2024.
"Surface Energy Data for Cellulose acetate, CAS # 9004-35-7", Diversified Enterprises, 2009, 1 page.
"TUBE Definition & Meaning" Merriam Webster Dictionary, 2025, <https://www.merriam-webster.com/dictionary/tube>.
Advisory Action for U.S. Appl. No. 16/452,258 mailed May 5, 2025.
Advisory Action for U.S. Appl. No. 17/378,015 mailed Oct. 28, 2025.
Advisory Action for U.S. Appl. No. 17/394,055 mailed Jan. 9, 2026.
Advisory Action for U.S. Appl. No. 17/446,256 mailed Nov. 6, 2025.
Advisory Action for U.S. Appl. No. 17/446,654 mailed Feb. 28, 2025.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/653,314 mailed Apr. 8, 2025.
Advisory Action for U.S. Appl. No. 17/655,464 mailed Feb. 25, 2025.
Advisory Action for U.S. Appl. No. 17/664,487 mailed Apr. 24, 2025.
Corrected Notice of Allowability for U.S. Appl. No. 17/444,792 mailed Jun. 24, 2025.
Corrected Notice of Allowability for U.S. Appl. No. 17/653,314 mailed Oct. 29, 2025.
Corrected Notice of Allowability for U.S. Appl. No. 17/808,354 mailed Nov. 25, 2025.
Corrected Notice of Allowability for U.S. Appl. No. 17/996,253 mailed Apr. 28, 2025.
Corrected Notice of Allowability for U.S. Appl. No. 18/134,857 mailed Mar. 14, 2025.
Corrected Notice of Allowability for U.S. Appl. No. 18/260,122 mailed Aug. 11, 2025.
Di Mauro, et al., "Penile length and circumference dimensions: A large study in young Italian men" Reconstructive Urology, Men's

(56) References Cited

OTHER PUBLICATIONS

Health Working Parties of the European Association of Urology (EAU) Young Academic Urologists (YAU). pp. 1-7, Mar. 8, 2021.
Final Office Action for U.S. Appl. No. 17/051,600 mailed Aug. 6, 2025.
Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/446,256 mailed Jun. 11, 2025.
Final Office Action for U.S. Appl. No. 17/446,654 mailed Dec. 22, 2025.
Final Office Action for U.S. Appl. No. 17/597,408 mailed Mar. 24, 2025.
Final Office Action for U.S. Appl. No. 17/614,173 mailed May 20, 2025.
Final Office Action for U.S. Appl. No. 17/625,941 mailed Feb. 18, 2025.
Final Office Action for U.S. Appl. No. 17/628,411 mailed Apr. 30, 2025.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/653,920 mailed Apr. 24, 2025.
Final Office Action for U.S. Appl. No. 17/664,487 mailed Jan. 5, 2026.
Final Office Action for U.S. Appl. No. 17/756,201 mailed Dec. 30, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/809,083 mailed Jan. 23, 2026.
Final Office Action for U.S. Appl. No. 17/907,125 mailed Apr. 30, 2025.
Final Office Action for U.S. Appl. No. 17/929,887, filed Jan. 13, 2026.
Final Office Action for U.S. Appl. No. 18/003,029 mailed Nov. 26, 2025.
Final Office Action for U.S. Appl. No. 18/006,807 mailed Dec. 23, 2025.
Final Office Action for U.S. Appl. No. 18/042,842 mailed Jan. 27, 2026.
Final Office Action for U.S. Appl. No. 18/043,618 mailed Nov. 26, 2025.
Final Office Action for U.S. Appl. No. 18/139,523 mailed May 8, 2025.
Final Office Action for U.S. Appl. No. 18/164,800 mailed Dec. 5, 2025.
Final Office Action for U.S. Appl. No. 18/247,986 mailed Jan. 7, 2026.
Final Office Action for U.S. Appl. No. 18/265,736 mailed Dec. 1, 2025.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
International Search Report and Written Opinion from International Application No. PCT/US2023/031432 mailed Feb. 29, 2024.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/053681 mailed Jan. 27, 2025.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
Issue Notification for U.S. Appl. No. 16/433,773 mailed Jan. 21, 2026.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,585 mailed Mar. 26, 2025.
Issue Notification for U.S. Appl. No. 17/444,792 mailed Jun. 25, 2025.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/597,673 mailed Jun. 4, 2025.
Issue Notification for U.S. Appl. No. 17/646,771 mailed Mar. 19, 2025.
Issue Notification for U.S. Appl. No. 17/653,920 mailed Oct. 22, 2025.
Issue Notification for U.S. Appl. No. 17/663,330 mailed Feb. 26, 2025.
Issue Notification for U.S. Appl. No. 17/749,340 mailed May 28, 2025.
Issue Notification for U.S. Appl. No. 17/755,236 mailed Oct. 29, 2025.
Issue Notification for U.S. Appl. No. 17/758,316 mailed Jun. 25, 2025.
Issue Notification for U.S. Appl. No. 17/907,125 mailed Dec. 30, 2025.
Issue Notification for U.S. Appl. No. 17/996,064 mailed Nov. 5, 2025.
Issue Notification for U.S. Appl. No. 17/996,155 mailed Oct. 8, 2025.
Issue Notification for U.S. Appl. No. 17/996,253 mailed Oct. 29, 2025.
Issue Notification for U.S. Appl. No. 17/996,468 mailed Nov. 26, 2025.
Issue Notification for U.S. Appl. No. 18/007,105 mailed Oct. 1, 2025.
Issue Notification for U.S. Appl. No. 18/044,413 mailed Dec. 30, 2025.
Issue Notification for U.S. Appl. No. 18/134,857 mailed May 28, 2025.
Issue Notification for U.S. Appl. No. 18/140,751 mailed Feb. 12, 2025.
Issue Notification for U.S. Appl. No. 18/260,122 mailed Nov. 12, 2025.
Issue Notification for U.S. Appl. No. 18/415,080 mailed Apr. 9, 2025.
Issue Notification for U.S. Appl. No. 18/426,795 mailed Feb. 19, 2025.
Issue Notification for U.S. Appl. No. 18/584,002 mailed Apr. 16, 2025.
Non-Final Office Action for U.S. Appl. No. 16/433,773 mailed Feb. 28, 2025.
Non-Final Office Action for U.S. Appl. No. 16/452,258 mailed Sep. 24, 2025.
Non-Final Office Action for U.S. Appl. No. 17/051,600 mailed Feb. 28, 2025.
Non-Final Office Action for U.S. Appl. No. 17/378,015 mailed Dec. 12, 2025.
Non-Final Office Action for U.S. Appl. No. 17/394,055 mailed Mar. 13, 2025.
Non-Final Office Action for U.S. Appl. No. 17/394,055 mailed Mar. 19, 2025.

(56) References Cited

OTHER PUBLICATIONS

Non-Final Office Action for U.S. Appl. No. 17/446,256 mailed Dec. 2, 2025.
Non-Final Office Action for U.S. Appl. No. 17/446,654 mailed May 1, 2025.
Non-Final Office Action for U.S. Appl. No. 17/451,354 mailed Mar. 19, 2025.
Non-Final Office Action for U.S. Appl. No. 17/595,747 mailed Jun. 12, 2025.
Non-Final Office Action for U.S. Appl. No. 17/614,173 mailed Dec. 29, 2025.
Non-Final Office Action for U.S. Appl. No. 17/628,411 mailed Dec. 22, 2025.
Non-Final Office Action for U.S. Appl. No. 17/631,619 mailed Mar. 19, 2025.
Non-Final Office Action for U.S. Appl. No. 17/635,866 mailed Jul. 29, 2025.
Non-Final Office Action for U.S. Appl. No. 17/645,821 mailed Mar. 31, 2025.
Non-Final Office Action for U.S. Appl. No. 17/653,314 mailed May 8, 2025.
Non-Final Office Action for U.S. Appl. No. 17/655,464 mailed Mar. 20, 2025.
Non-Final Office Action for U.S. Appl. No. 17/664,487 mailed May 19, 2025.
Non-Final Office Action for U.S. Appl. No. 17/754,736 mailed Mar. 31, 2025.
Non-Final Office Action for U.S. Appl. No. 17/756,201 mailed Apr. 24, 2025.
Non-Final Office Action for U.S. Appl. No. 17/758,152 mailed Apr. 8, 2025.
Non-Final Office Action for U.S. Appl. No. 17/759,587 mailed Jan. 26, 2026.
Non-Final Office Action for U.S. Appl. No. 17/759,697 mailed Sep. 17, 2025.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/912,147 mailed May 29, 2025.
Non-Final Office Action for U.S. Appl. No. 17/929,887 mailed Jun. 25, 2025.
Non-Final Office Action for U.S. Appl. No. 17/930,238 mailed Jun. 30, 2025.
Non-Final Office Action for U.S. Appl. No. 17/933,590 mailed Jul. 29, 2025.
Non-Final Office Action for U.S. Appl. No. 17/996,064 mailed Mar. 6, 2025.
Non-Final Office Action for U.S. Appl. No. 17/996,556 mailed Dec. 22, 2025.
Non-Final Office Action for U.S. Appl. No. 18/003,029 mailed Apr. 18, 2025.
Non-Final Office Action for U.S. Appl. No. 18/006,807 mailed May 29, 2025.
Non-Final Office Action for U.S. Appl. No. 18/042,842 mailed May 22, 2025.
Non-Final Office Action for U.S. Appl. No. 18/043,618 mailed May 19, 2025.
Non-Final Office Action for U.S. Appl. No. 18/115,444 mailed Oct. 22, 2025.
Non-Final Office Action for U.S. Appl. No. 18/139,523 mailed Nov. 19, 2025.
Non-Final Office Action for U.S. Appl. No. 18/150,360 mailed Nov. 5, 2025.
Non-Final Office Action for U.S. Appl. No. 18/164,800 mailed Apr. 25, 2025.
Non-Final Office Action for U.S. Appl. No. 18/246,121 mailed Jan. 22, 2026.
Non-Final Office Action for U.S. Appl. No. 18/247,986 mailed Jun. 4, 2025.
Non-Final Office Action for U.S. Appl. No. 18/249,577 mailed Nov. 17, 2025.
Non-Final Office Action for U.S. Appl. No. 18/254,638 mailed Nov. 17, 2025.
Non-Final Office Action for U.S. Appl. No. 18/259,626 mailed Jan. 30, 2026.
Non-Final Office Action for U.S. Appl. No. 18/259,626 mailed Jul. 11, 2025.
Non-Final Office Action for U.S. Appl. No. 18/260,394, filed Jan. 13, 2026.
Non-Final Office Action for U.S. Appl. No. 18/264,004 mailed May 15, 2025.
Non-Final Office Action for U.S. Appl. No. 18/264,278 mailed Nov. 10, 2025.
Non-Final Office Action for U.S. Appl. No. 18/265,736 mailed Jul. 1, 2025.
Non-Final Office Action for U.S. Appl. No. 18/548,152 mailed Sep. 16, 2025.
Non-Final Office Action for U.S. Appl. No. 18/553,625 mailed Oct. 2, 2025.
Non-Final Office Action for U.S. Appl. No. 18/556,945 mailed Dec. 19, 2025.
Non-Final Office Action for U.S. Appl. No. 18/757,964 mailed Aug. 20, 2025.
Notice of Allowance for U.S. Appl. No. 16/433,773 mailed Oct. 10, 2025.
Notice of Allowance for U.S. Appl. No. 17/051,399 mailed Nov. 17, 2025.
Notice of Allowance for U.S. Appl. No. 17/051,600 mailed Jan. 5, 2026.
Notice of Allowance for U.S. Appl. No. 17/444,792 mailed Mar. 28, 2025.
Notice of Allowance for U.S. Appl. No. 17/451,345 mailed Jun. 24, 2025.
Notice of Allowance for U.S. Appl. No. 17/451,354 mailed Nov. 18, 2025.
Notice of Allowance for U.S. Appl. No. 17/596,629 mailed May 27, 2025.
Notice of Allowance for U.S. Appl. No. 17/597,673 mailed Feb. 26, 2025.
Notice of Allowance for U.S. Appl. No. 17/625,941 mailed Nov. 13, 2025.
Notice of Allowance for U.S. Appl. No. 17/645,821 mailed Nov. 24, 2025.
Notice of Allowance for U.S. Appl. No. 17/653,137 mailed Oct. 22, 2025.
Notice of Allowance for U.S. Appl. No. 17/653,314 mailed Oct. 20, 2025.
Notice of Allowance for U.S. Appl. No. 17/653,920 mailed Jul. 9, 2025.
Notice of Allowance for U.S. Appl. No. 17/749,340 mailed Feb. 14, 2025.
Notice of Allowance for U.S. Appl. No. 17/754,736 mailed Jan. 28, 2026.
Notice of Allowance for U.S. Appl. No. 17/755,236 mailed Jul. 17, 2025.
Notice of Allowance for U.S. Appl. No. 17/758,316 mailed Mar. 24, 2025.
Notice of Allowance for U.S. Appl. No. 17/759,697 mailed Jan. 30, 2026.
Notice of Allowance for U.S. Appl. No. 17/808,354 mailed Nov. 12, 2025.
Notice of Allowance for U.S. Appl. No. 17/878,268 mailed Oct. 15, 2025.
Notice of Allowance for U.S. Appl. No. 17/907,125 mailed Sep. 26, 2025.
Notice of Allowance for U.S. Appl. No. 17/912,147 mailed Dec. 3, 2025.

(56) References Cited

OTHER PUBLICATIONS

Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,253 mailed Jul. 11, 2025.
Notice of Allowance for U.S. Appl. No. 17/996,468 mailed Apr. 14, 2025.
Notice of Allowance for U.S. Appl. No. 17/996,468 mailed Jul. 15, 2025.
Notice of Allowance for U.S. Appl. No. 18/007,105 mailed Jun. 17, 2025.
Notice of Allowance for U.S. Appl. No. 18/044,413 mailed Sep. 16, 2025.
Notice of Allowance for U.S. Appl. No. 18/134,857 mailed Feb. 20, 2025.
Notice of Allowance for U.S. Appl. No. 18/260,122 mailed Jul. 30, 2025.
Notice of Allowance for U.S. Appl. No. 18/264,004 mailed Jan. 30, 2026.
Restriction Requirement for U.S. Appl. No. 17/625,887 mailed Sep. 2, 2025.
Restriction Requirement for U.S. Appl. No. 17/755,236 mailed Apr. 24, 2025.
Restriction Requirement for U.S. Appl. No. 17/929,887 mailed Mar. 10, 2025.
Restriction Requirement for U.S. Appl. No. 17/930,238 mailed Apr. 17, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/260,394 mailed Jul. 25, 2025.
Restriction Requirement for U.S. Appl. No. 18/294,370 mailed Nov. 26, 2025.
Restriction Requirement for U.S. Appl. No. 18/294,403 mailed Jan. 27, 2026.
Restriction Requirement for U.S. Appl. No. 18/335,579 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/558,502 mailed Jan. 29, 2026.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/662,216 mailed Nov. 26, 2025.
Restriction Requirement for U.S. Appl. No. 19/237,638 mailed Dec. 18, 2025.
Supplemental Notice of Allowance for U.S. Appl. No. 17/597,673 mailed Apr. 10, 2025.
U.S. Appl. No. 17/596,629, filed Dec. 15, 2021.
U.S. Appl. No. 18/034,902, filed May 2, 2023.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/353,151, filed Oct. 8, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150, filed Dec. 12, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/491,481, filed Dec. 9, 2025.
U.S. Appl. No. 19/494,631, filed Dec. 18, 2025.
U.S. Appl. No. 63/564,696, filed Mar. 13, 2024.

* cited by examiner

APPARATUS AND METHODS FOR RECEIVING DISCHARGED URINE

CROSS-REFERENCE TO RELATED APPLICATIONS

This application is a U.S. Nationalization of PCT International Application No. PCT/US2020/065234 filed on 16 Dec. 2020, which claims priority to U.S. Provisional Patent Application No. 62/949,187 filed on Dec. 17, 2019, the disclosure of which is incorporated herein, in its entirety, by this references.

BACKGROUND

In various circumstances, a person may have limited or impaired mobility such that typical urination processes are challenging or impossible. For example, a person may experience or have a disability that impairs mobility. A person may have restricted travel conditions such as those experienced by pilots, drivers, and workers in hazardous areas. Additionally, sometimes urine collection is needed for monitoring purposes or clinical testing.

Urinary catheters, such as a Foley catheter, can be used to address some of these circumstances, such as incontinence. Unfortunately, however, urinary catheters can be uncomfortable, painful, and can lead to complications, such as infections. Additionally, bed pans, which are receptacles used for the toileting of bedridden patients, such as those in a health care facility, are sometimes used. Bed pans, however, can be prone to discomfort, spills, and other hygiene issues.

Males who suffer the most severe consequences of urinary incontinence, such as discomfort, rashes, and sores are typically elderly and often bedbound. They also require continuous assistance to maintain hygiene. Characteristics often found in these patients: they typically lay on their back, the size of the penis often decreases with age, skin rolls containing fat tissue cause the penis to recede, often pointing upward while in a laying position, patients have difficulty reaching the penis and manipulating devices. A urine capture device should be designed with reference to these characteristics.

SUMMARY

Embodiments are directed to urine collection devices suitable for collecting and transporting urine away from the body of a person. In an embodiment of the present disclosure, a urine collection device is disclosed. The urine collection device can include a receptacle and an elongate member. The receptacle can define an interior volume. The receptacle can be configured to receive a penis of a user. The receptacle can include a fluid permeable layer and at least one channel configured to direct urine within the interior volume toward a passage formed within the receptacle. The passage can be configured to extract urine from the receptacle. The elongate member can be coupled to the receptacle. The elongate member can have a distal end and a proximal end. The elongate member can include a curved surface positioned between the distal end and the proximal end. The curved surface can be configured to abut a perineum of the user.

In another embodiment of the present disclosure, a method for transporting urine away from the body is disclosed. The method can include positioning a receptacle of a urine collection device to abut one or more regions about a penis of a user. The method can also include positioning an elongate member of the urine collection device between the legs of the user. The elongate member can extend between the thighs of the user. The elongate member can be positioned proximal to a perineum of the user. The elongate member can retain the receptacle of the urine collection device in a fixed position. The method can also include receiving urine within the receptacle of the urine collection device. The method can further include directing the urine, using at least one channel formed within the receptacle of the urine collection device, to a passage within the receptacle of the urine collection device. The method can also include removing the urine from the receptacle through the passage.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
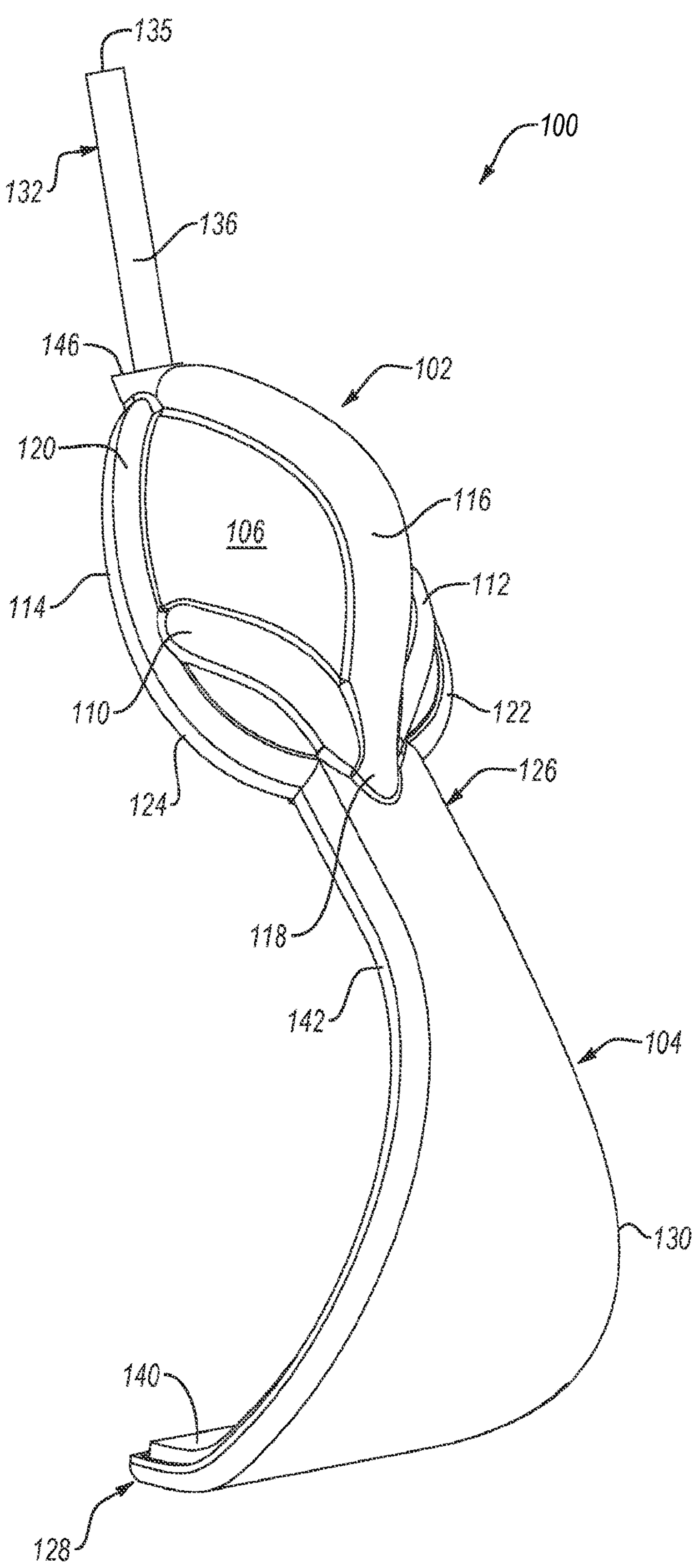
FIG. 1A is an isometric view of a urine collection device, according to an embodiment.

Embodiments are directed to urine collection devices suitable for collecting and transporting urine away from the body of a person. Embodiments of a urine collection device may include a receptacle and an elongate member. The receptacle can include an outer wall or outer surface, which defines a volume within the receptacle. The volume can be configured to receive a penis of the user and position the outer surface proximate to one or more regions about the penis of the user. The receptacle can include and/or house a plurality of layers, for example, one or more fluid permeable layers, one or more absorbent layers, one or more hydrophobic layers, one or more wicking layers, and so on. The receptacle can include one or more channels formed or otherwise coupled to the receptacle within the volume. Each channel can direct the flow of urine within the volume to a desired location within the volume. For example, the channels can direct the flow of urine to a passage configured to extract the urine from the receptacle. The passage can be a conduit or channel formed within or attached to the receptacle. In some embodiments, the passage can be configured to retain a tube coupled to a vacuum source which extracts urine from the receptacle. One suitable non-limiting example of a vacuum source that can be used is the DryDoc Vacuum Station, available from PureWick, Inc.

Although the device can receive a portion of the user's penis within the receptacle, the device can be equally beneficial in collecting urine from a user without requiring a portion of the user's penis to be received within the receptacle. For example, patients having hidden anatomy, such as a buried penis, can still utilize the device despite having substantially inaccessible anatomy.

The elongate member can include a distal end and a proximal end. The proximal end of the elongate member can be coupled to the receptacle. The distal end of the elongate member can form a planar surface. The planar surface can abut a portion of the user's body to retain the receptacle in a fixed position relative to the user, as described in more detail herein. The elongate member can include a curved portion or curved surface spanning some distance between the distal and proximal ends. In some embodiments, the curved surface can be modifiable to match the contour of the user's perineum. In an embodiment, the urine collection device can be utilized without strapping, adhering, or otherwise affixing the device to the patient. For example, the elongate member of the device can be positioned between a user's (e.g., a patient) thighs to retain the receptacle in a position abutting one or more regions about the penis of the user. The width of the elongate member can vary from the proximal to the distal end. For example, a section of the elongate member configured to be retained between the user's legs can be narrower than a section of the elongate member configured to be positioned proximal to the user's buttocks or lower back.

In some embodiments, a method for transporting urine away from the body may include positioning a receptacle of a urine collection device to abut one or more regions about a penis of the user. The method can include positioning an elongate member of the urine collection device between the legs of the user. For example, the elongate member can be positioned between the thighs of the user and proximal to the perineum of the user. By positioning the elongate member between the legs of the user, the position of the receptacle relative to the user's penis can also be maintained without adhering or otherwise attaching the receptacle to the user's skin. The method can also include receiving expelled urine from the user into the receptacle and directing the urine to the passage using at least one channel formed within the receptacle. The urine can thereafter be extracted from the receptacle via the passage using, for example, a vacuum system or suction device.

Figure 1B:
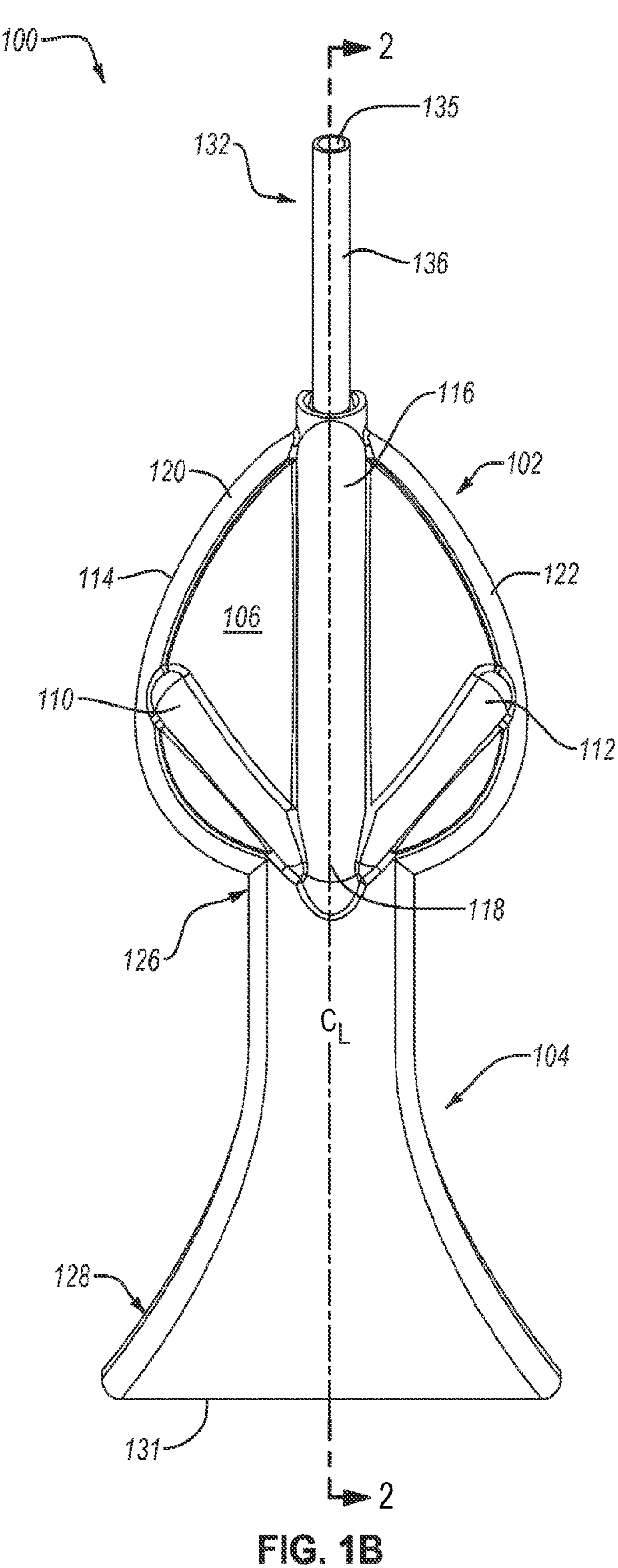
FIG. 1B is a front view of the urine collection device shown in FIG. 1A.
Figure 1C:
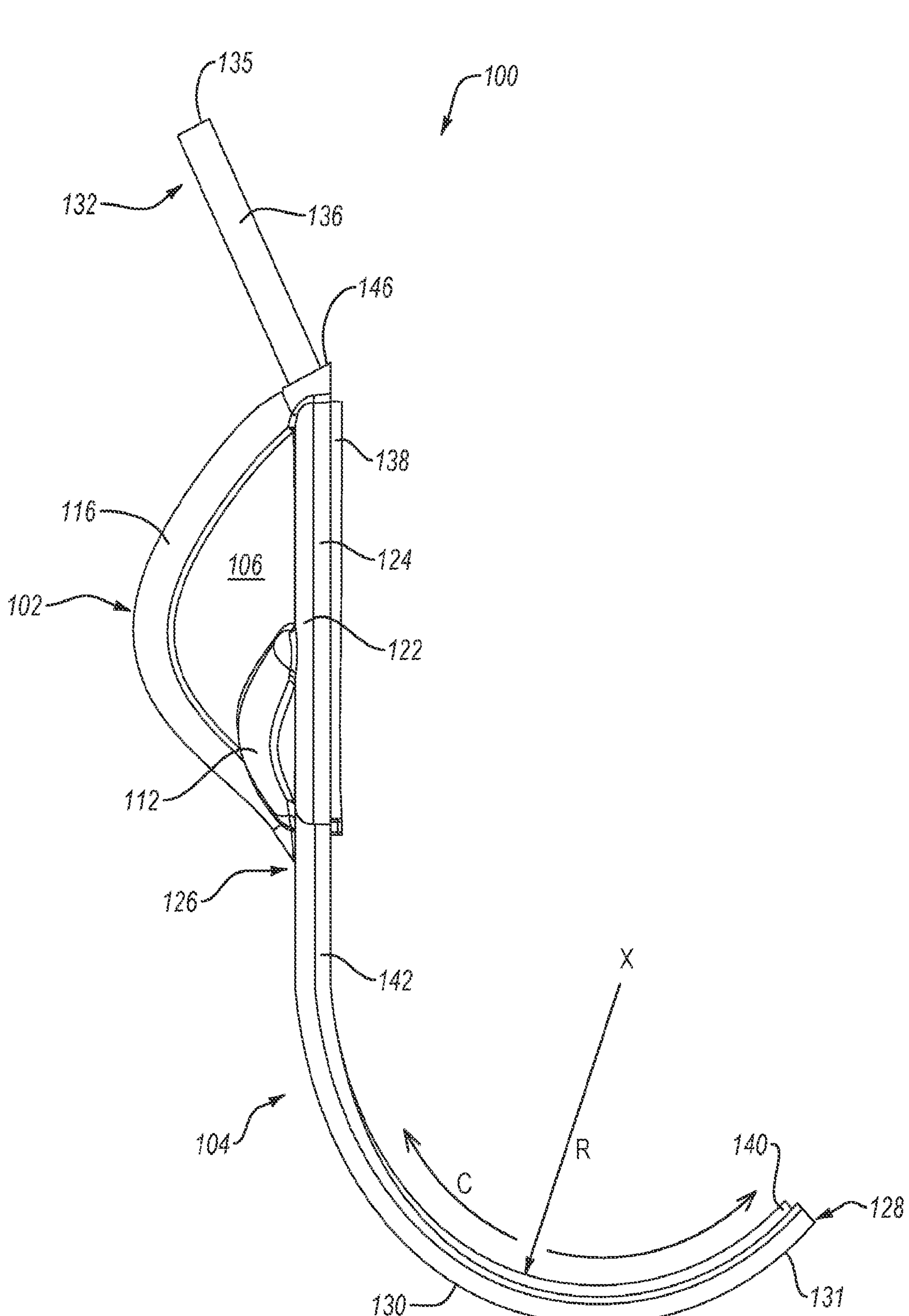
FIG. 1C is a side view of the urine collection device shown in FIG. 1A.

FIGS. 1A-1C are respective isometric, front, and side views of a urine collection device 100, according to an embodiment. The urine collection device 100 includes a receptacle 102 and an elongate member 104. The receptacle 102 has semi-elliptically shaped perimeter. The exterior surface 106 of the receptacle 102 forms a generally convex exterior while an interior surface 108 of the receptacle 102 forms a generally concave interior (see FIG. 3). The receptacle 102 also forms or defines an interior volume. While the receptacle 102 is depicted as semi-elliptical, other embodiments of the receptacle 102 can be cylindrical, spherical, cubic, a combination thereof, or any other three-dimensional shape capable of defining an internal volume.

The receptacle 102 can be formed of any suitable fluid impermeable materials, such as a fluid impermeable polymer (e.g., silicone, polypropylene, polyethylene, polyethylene terephthalate, polyurethane, a polycarbonate, polyvinyl chloride, latex, silicone, etc.), a metal or alloy layer or film, another suitable material, or combinations thereof.

The receptacle 102 defines one or more channels 110, 112. The channels 110, 112 can protrude from the exterior surface 106 of the receptacle 102 and form recesses on the interior surface 108 of the receptacle 102. The channels 110, 112 can be configured to direct or guide the flow of urine within the receptacle 102 to a passage 116. In an embodiment, the channels 110, 112 can extend from a periphery 114 of the receptacle 102 and terminate at a collection region 118 wherein the channels 110, 112 intersect with the passage 116. During use, the receptacle 102 is positioned such that urine expelled from the patient contacts the interior surface 108 of the receptacle 102 and flows along the channels 110, 112 and into the collection region 118. For example, the receptacle 102 can be inclined such that the collection region 118 is at a lower elevation or height than the rest of the receptacle 102. Thus, gravitational force can be used to drive the urine through the channels 110, 112.

Additionally or alternatively, the receptacle 102 can form or otherwise define channels 120, 122 about the periphery 114 of the receptacle 102. Channels 120, 122 can be configured to direct or guide the flow of urine within the receptacle 102 to the collection region 118. The channels 120, 122 can be integrally formed with one or more walls 124 defined by the receptacle 102. The one or more walls 124 can extend around at least a portion of the periphery 114 of the receptacle 102.

The elongate member 104 can be integrally formed or otherwise molded with the receptacle 102 such that the elongate member 104 and receptacle 102 are a unitary structure. For example, the elongate member 104 and receptacle 102 can be molded utilizing a single material, multiple materials (e.g., multi-material injection molding), a single shot, or multiple shots. In other embodiments, the elongate member 104 can be coupled or otherwise attached to the receptacle 102. For example, a proximal end 126 of the elongate member 104 can be adhered, fastened, or interlocked with the receptacle 102. The proximal end 126 of the elongate member 104 can be positioned proximal to or abutting the collection region 118. As illustrated in FIGS. 1A-1C, the passage 116, channels 110, 112, and collection region 118 extend into the proximal end of the elongate member 104.

The elongate member 104 extends some length from the receptacle 102, curves to conform to a patient's perineum, and terminates proximal to the patient's buttocks or lower back. The length of the elongate member 104 can vary, for example, relative to the size and dimension of the patient. The elongate member 104 can be conformable or otherwise compliant such that a curved portion 130 of the elongate member 104 can be manipulated to accommodate the perineum shape of a particular patient. Due to the arc or curvature of the curved portion 130, the receptacle 102 can be positioned over the penis while a distal end 128 of the elongate member 104 can be positioned between a part of the patient's body (e.g., a buttocks or lower back) and a support structure being used by the patient (e.g., a bed, chair, etc.). Thus, retaining the position of the receptacle 102 over the user's penis without necessitating the use of adhesives or straps.

The elongate member 104 can be made out of similar materials as the receptacle 102. For example, the elongate member can be formed of any suitable fluid impermeable materials, such as a fluid impermeable polymer (e.g., silicone, polypropylene, polyethylene, polyethylene terephthalate, polyurethane, a polycarbonate, polyvinyl chloride, latex, silicone, etc.), a metal or alloy layer or film, another suitable material, or combinations thereof.

The elongate member 104 can be reconfigurable to accommodate patients of varying sizes and shapes. In other words, the elongate member 104 can be deformable and thereby allow the radius R or circumference C of the curved section 130 to be adjusted or otherwise manipulated. For example, the elongate member 104 can be over-molded or coupled to a semi-rigid structure (not shown) which bends, twists, or otherwise deforms and thereafter retains the elongate member 104 in a deformed state. The semi-rigid structure can extend some length between the proximal end 126 and distal end 128 of the elongate member 104. In an embodiment, the semi-rigid structure can be a wire frame comprising members which span one or more directions relative to a centerline $C_L$ of the elongate member 104.

The width of the elongate member 104 can be narrower near the proximal end 126 and wider near the distal end 128 to accommodate the curvature of the patient's thighs or space between a patient's thighs while the patient is sitting or in a reclined state. In some embodiments, the width of the elongate member 104 remains constant near the proximal end 126 and flares or broadens through the curved portion 130 of the elongate member 104 (as depicted in FIGS. 1C and 1B). Varying the width of the elongate member 104 can be beneficial, for example, to more comfortably and ergonomically retain the device 100 between the patient's thighs. The distal end 128 of the elongate member 104 defines a planar surface 131 which can be disposed between the patient and a support surface on which the patient is positioned (e.g., a bed, chair, etc.). Compressive forces generated by the weight of the patient and the support structure supporting the patient are applied to the planar surface 131 to retain the position of the device 100 relative to the patient. For example, the planar surface 131 can engage with a larger surface area of the patient's buttocks and/or lower back to provide a secondary structure for retaining the relative position of the receptacle relative to the user's penis (i.e., preventing the device 100 from moving once placed on the patient).

Figure 2:
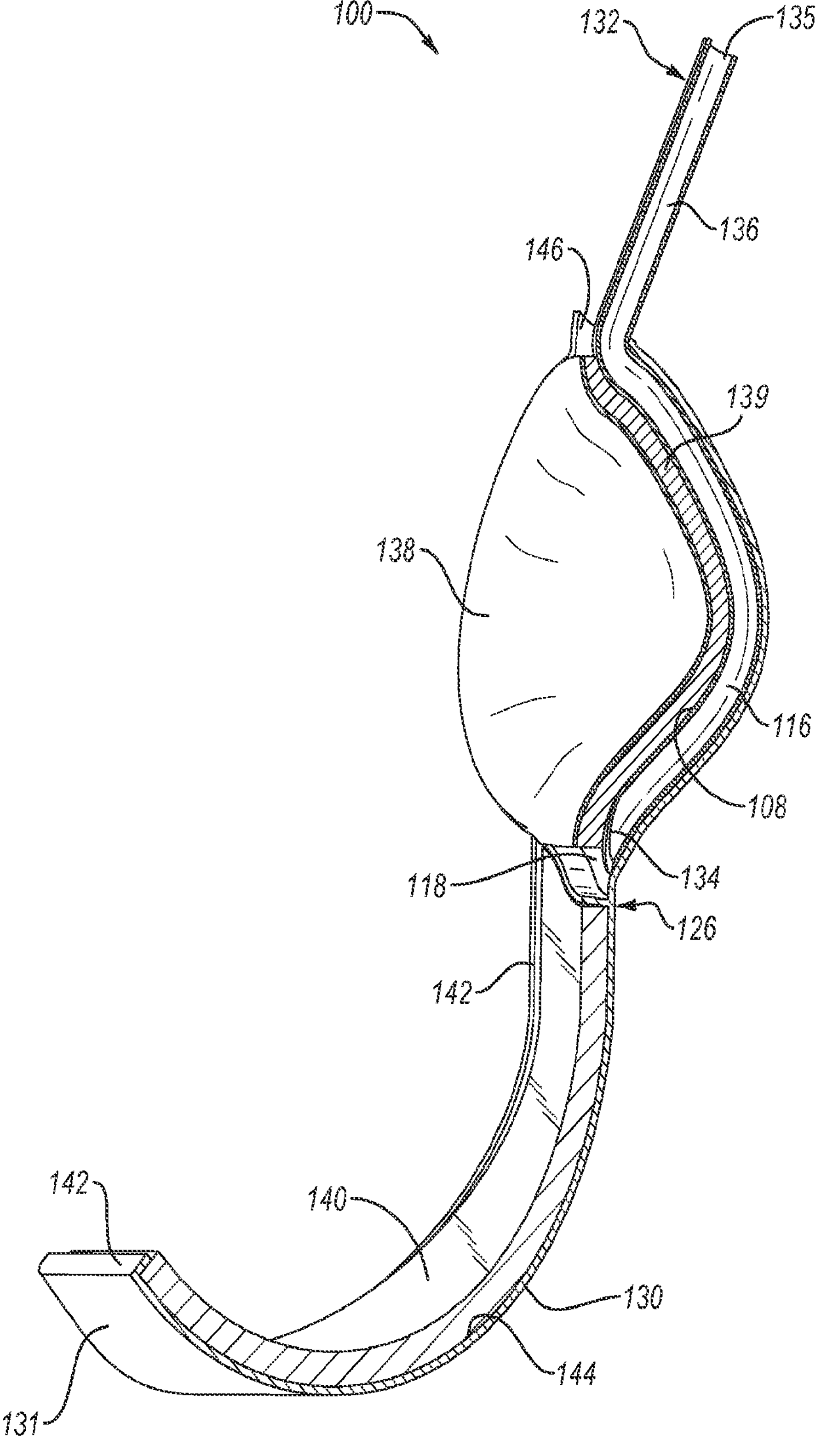
FIG. 2 is a schematic cross-section view of the urine collection device taken through the section lines 2-2 of FIG. 1B.

FIG. 2 is a section view of the urine collection device 100 taken through section line 2-2 shown in FIG. 1B, according to an embodiment. The device 100 includes a receptacle 102, an elongate member 104, and a tube 132. The tube 132 can occupy at least a portion of the passage 116. For example, the tube 132 can be inserted within the passage 116 and occupy at least the length of the passage 116, at least half the length of the passage 116, or less than half the length of the passage 116. The tube 132 can include an inlet 134, an outlet 135, and a body 136. The inlet 134 is positioned proximal to the collection region 118 (as depicted in FIG. 2) and the body is at least partially positioned within the passage 116. In other embodiments, the body 136 of the tube 132 need not extend along the passage 116 and through inner volume. Instead, the tube 132 can be placed in liquid communication with the passage 116 at or near the periphery 114 of the receptacle 102. For example, the inlet 134 of the tube 132 can be positioned within the passage 116 while the body 136 of the tube 132 remains outside the receptacle 102. The outlet 135 of the tube 132 is operably coupled to a vacuum pump or suction device (suction device 412 depicted in FIG. 4). The tube 132 can be utilized to extract urine expelled into the receptacle 102 by the patient. For example, the tube 132 can be a component of a vacuum source which uses negative pressure to extract urine from the device 100. One suitable non-limiting example of a vacuum source that can be used is the DryDoc Vacuum Station, available from PureWick, Inc.

In some embodiments, the urine collection device 100 can include a fluid permeable layer 138. The fluid permeable layer 138 cover one or more surfaces of the device 100. The fluid permeable layer 138 can be non-abrasive to mitigate or prevent irritation to any portion of the patient's skin which contacts the fluid permeable layers 138. The fluid permeable layer 138 can include multiple layers of material, such as, hydrophobic or wicking layers having varied permeable properties. The fluid permeable layer 138 can include any material that can wick fluid. For example, the fluid permeable layer 138 can include fabric, such as a gauze (e.g., a silk, linen, polyester, or cotton gauze), another soft fabric (e.g., jersey knit fabric or the like), or another smooth fabric (e.g., rayon, satin, or the like). In some examples, the fluid permeable layer 138 can include an open cell foam. Forming the fluid permeable layer 138 from gauze, soft fabric, and/or smooth fabric can reduce chafing caused by the urine collection device 100. The fluid permeable layers 138 can additionally or alternatively be formed using one or more layers of polytetrafluoroethylene (PTFE) and/or spun plastic.

The fluid permeable layer 138 of the receptacle 102 can be coupled to, cover, disposed adjacent to, and/or being in fluid communication with a permeable support 139 positioned within the inner volume of the receptacle 102. For example, the fluid permeable layer 138 can be adhered to the permeable support 139. Similarly, the permeable support 139 can be adhered to the inner surface 108 of the receptacle 102 and the one or more walls 124 of the receptacle 102, as alternative to or in addition to being adhered to the permeable support 139. The fluid permeable layer 138 and the permeable support 139 can be positioned within the receptacle 102 such that the concaved contour defined by the inner surface 108 of the receptacle 102 is matched by the fluid permeable layer 138 and the permeable support 139. The permeable support 139, however, in some embodiments, may not be adhered to the channels 110, 112, 120, 122 of the receptacle 102 nor the collection region 118. The fluid permeable layer 138 can be removable in some examples by utilizing hook and loop fasteners to allow a replacement layer to be inserted and used within the device 100.

The permeable support 139 allows fluid such as, for example, urine, to flow through the fluid permeable layer 138, through the permeable support 139, and into the receptacle 102. In an embodiment, the permeable support 139 can be made of a rigid or flexible plastic. In an embodiment, the permeable support 139 can have any suitable shape and be formed of any suitable material. Additionally or alternatively, the permeable support 139 can be formed of aluminum, a composite of plastic and aluminum, some other metal and/or a composite of plastic and another metal. In some embodiments, the permeable support 139 can be formed of a natural material, such as, for example, plant fibers (e.g., Greener Clean manufactured by 3M®). The natural material can include openings that allow fluid to flow through the natural material. In some embodiments, the permeable support 139 can be formed of perforated coated paper, such as waxed paper.

The permeable support 139 can define one or more openings to allow for fluid flow from the fluid permeable layer 138 to the receptacle 102. In some embodiments, the permeable support 139 can include membrane supports (e.g., struts) extending across an opening such that the opening is divided into an array of distinct slot-shaped openings. The membrane supports can be used to support the fluid permeable layer 138. For example, the membrane supports can maintain the shape of the fluid permeable layer 138 such that urine flowing from the wearer contacts and travels through the fluid permeable layer 138. In some embodiments, the permeable support 139 can define several openings having a variety of shapes, such as a plurality of round openings. In some embodiments, the permeable support 139 can be formed of spun plastic (e.g., non-woven permeable nylon and polyester webbing) such that the permeable support 139 can have many openings. In some embodiments, the permeable support 139 can be formed of a porous material.

In an embodiment, the fluid permeable layer 138 allows fluid to flow through the material in a first direction but prevent fluid from flowing through the material in a second direction. For example, the fluid permeable layer 138 can allow urine to flow through the fluid permeable layer 138 and into the permeable support 139 while preventing or inhibiting urine from flowing back out of the permeable support 139 and onto the user's skin. In other words, the fluid permeable layer 138 can permit unidirectional fluid flow and thereby obstruct urine from leaking through the layer 138 and contacting the user's skin.

The fluid permeable layer 138 and the permeable support 109 include permeable material designed to wick or pass fluid therethrough. The permeable properties referred to herein may be wicking, capillary action, diffusion, or other similar properties or processes, and are referred to herein as "permeable" and/or "wicking." Such "wicking" may not include absorption of fluid into the wicking material. Put another way, substantially no absorption of fluid into the material may take place after the material is exposed to the fluid and removed from the fluid for a time. While no absorption is desired, the term "substantially no absorption" may allow for nominal amounts of absorption of fluid into the wicking material (e.g., absorbency), such as less than about 10 wt % of the dry weight of the wicking material, less than about 7 wt %, less than about 5 wt %, less than about 3 wt %, less than about 2 wt %, less than about 1 wt %, or less than about 0.5 wt % of the dry weight of the wicking material. Wicking material can include natural fibers. In such examples, the material may have a coating to prevent or limit absorption of fluid into the material, such as a water repellent coating.

The elongate member 104 can include a support layer 140 which interfaces a portion of the user's skin when the device 100 is being used. For example, the support layer 140 can abut one or more surfaces proximate to the perineum or buttocks of the user while the device 100 is in use. The support layer 140 of the elongate member 104 can be adhered or otherwise affixed to the elongate member 104. More specifically, the support layer 140 can be positioned between one or more walls 142 of the elongate member 104 and adhered to an inner surface 144 of the elongate member 104. The support layer 140 can be positioned adjacent to the inner surface 144 such that support matches or substantially matches the circumference C and radius R of the curved portion 130.

The support layer 140 can be non-abrasive to mitigate or prevent irritation to any portion of the patient's skin which contacts the support layer 140. The support layer 140 can also function as a deformable cushion or pad to provide additional comfort to the user. For example, in some embodiments, the support layer 140 can be a foam, cloth, or other material which is non-abrasive and deformable. The support layer 140 can be removable from the elongate member 104. For example, the support layer 140 can be coupled to the inner surface 144 of the elongate member 104 using hook and loop fasteners or other mechanisms configured to allow removal without damaging the device 100.

The support layer 140 can include multiple layers of material, such as, hydrophobic or non-absorptive layers. For example, the support layer 140 can include a non-absorptive foam. Additionally or alternatively, the support layer 140 can include fabric, such as a gauze (e.g., a silk, linen, polyester, or cotton gauze), another soft fabric (e.g., jersey knit fabric or the like), or another smooth fabric (e.g., rayon, satin, or the like). Forming the support layer 140 from non-absorptive material can reduce chafing caused by the urine collection device 100.

Figure 3:
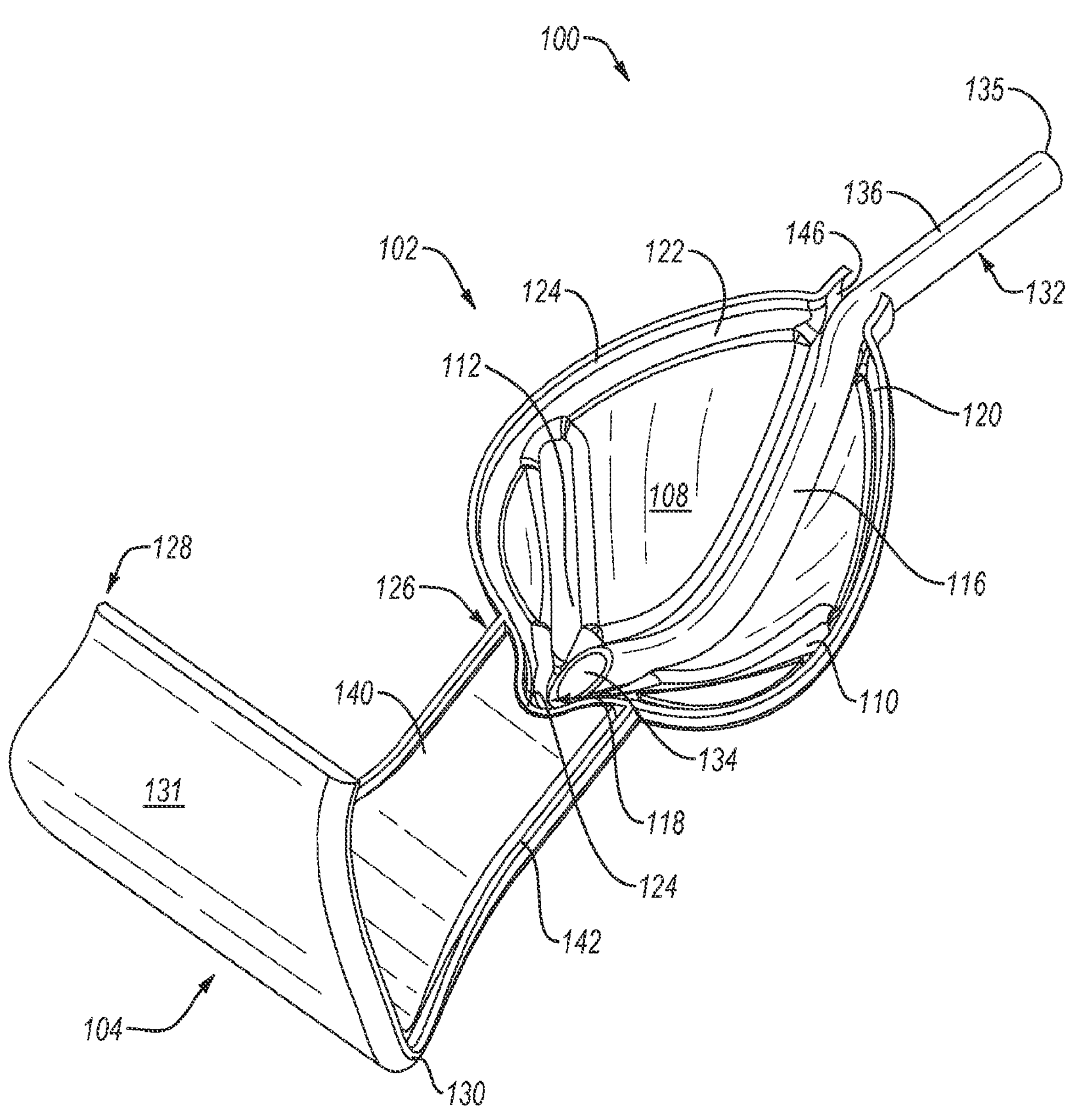
FIG. 3 is a rear isometric view of the urine collection device shown in FIG. 1A having a fluid permeable layer and a permeable support removed to expose an inner surface of a receptacle.

FIG. 3 depicts a rear view of the receptacle 102 having the fluid permeable layer 138 and the permeable support 139 removed. The passage 116 is configured to receive and retain a portion of the tube 132 against the inner surface 108 of the receptacle 102. For example, the passage 116 can have a c-shaped cross-section which flexes to receive and retain a portion of the body 136 of the tube 132. The body 136 of the tube 132 can be routed through one or more features of the receptacle 102. For example, the body 136 can be routed into the receptacle 102 through an opening or aperture 146 of the receptacle 102. The one or more side walls 124 and outer surface 106 of the receptacle 102 can define the aperture 146. The aperture 146 and the collection region 118 can be positioned on opposing sides of the receptacle 102. As depicted in FIG. 3, the body 136 of the tube 132 is received within the aperture 146 and thereafter bent to be received and retained by the passage 116. While the passage 116 is positioned at or near a geometric center of the receptacle 102 in FIG. 3, it should be appreciated that the passage 116 can be positioned anywhere within the inner volume of the receptacle 102 (e.g., abutting the one or more walls 124 and extending along a periphery 114 of the receptacle 102).

In other embodiments, the passage 116 can be have a circular cross-section with a diameter large enough to house the body 136 of the tube 132. In yet other embodiments, the passage 116 can form a conduit in liquid communication with the collection region 118 and the aperture 146. In this embodiment, the inlet 134 of the tube 132 can be received within the aperture 146 and a vacuum system can be used to extract urine from the collection region 118, through the passage 116, and into the inlet 134 of the tube 132.

An adhesive can be disposed on a portion of the inner surface 108 of the receptacle 102. The adhesive can adhere or otherwise affix the permeable support 139 to the inner surface 108 of the receptacle 102. However, the channels 110, 112, passage 116, and one or more walls 124 can be free of adhesive.

The channels 110, 112 and passage 116 extend some length within the receptacle 102 and terminate at the collection region 118. The collection region 118 is positioned within the receptacle 102 such that gravity draws or pulls urine within the cup along the one or more channels 110, 112 and into the collection region 118. For example, the collection region 118 can be positioned at a lower elevation (e.g., relative height) than the one or more channels 110, 112 such that gravity forces the urine into the collection region 118. The collection region 118 can be defined by one or more features within the receptacle 102. For example, as depicted in FIG. 3, the collection region 118 can be defined by the wall 124, channels 110, 112, and the passage 116.

Figure 4:
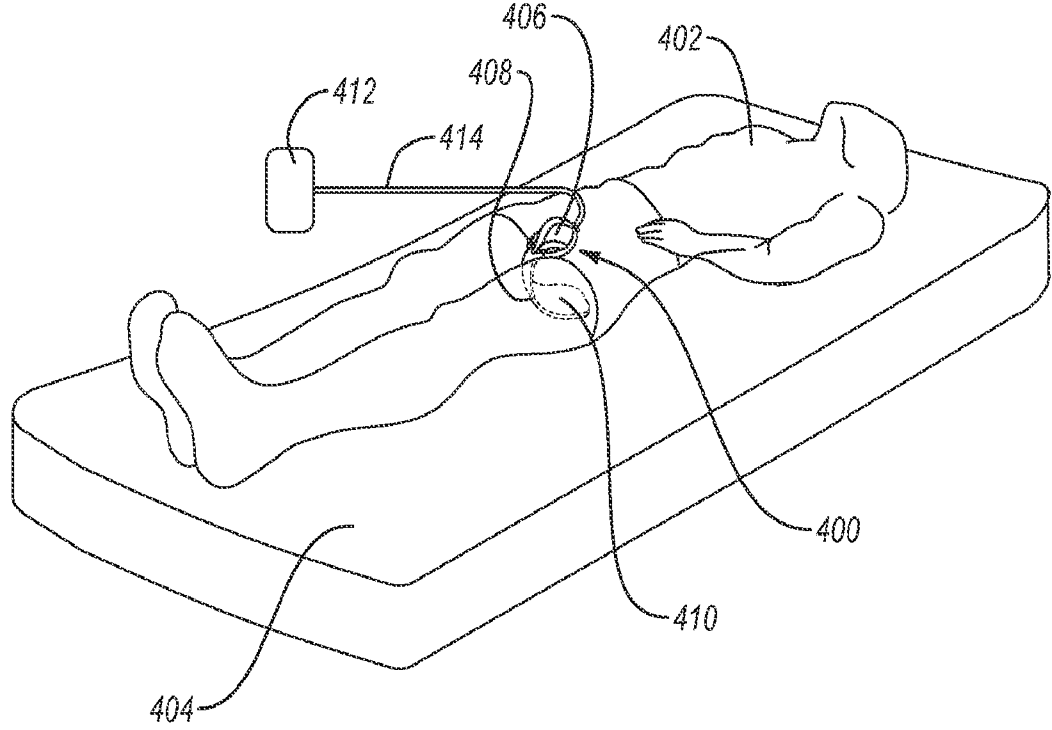
FIG. 4 is a side view of the urine collection device shown in FIG. 1A positioned on a patient.

FIG. 4 depicts a urine collection device 400 positioned on a patient 402, according to an embodiment. The patient 402 is positioned on a support structure, for example, a hospital bed 404. It should be appreciated that the urine collection device 400 can be utilized by a patient being supported in a plurality of resting positions (e.g., supine, semi-supine, sitting upright, reclined, etc.). As previously described and shown in FIG. 4, the urine collection device 400 is positioned proximal to the user's body 402. More specifically, a receptacle 406 of the device 400 is position to abut regions about the user's penis while an elongate member 408 of the device 400 can be positioned between the user's thighs and/or legs. The device 400 thereby utilizes the elongate member 408 to retain the device 400 in a fixed position relative to the user 402. Additionally or alternatively, a planar surface 410 of the elongate member 408 can abut the user's buttocks and/or lower back to retain the device 400 in a fixed position relative to the user 402.

The position of the elongate member 408 between the user's thighs and abutting the user's lower back and/or buttocks retains the device 400 in a fixed position without requiring adhesives or other attachment means to adhere the device 400 to the patient 402. This is beneficial because adhesives can irritate the patient's skin by causing inflammation, soreness, infection, rashes, hives, and so on. Moreover, the device 400 can be exchanged or replaced without causing discomfort to the patient (e.g., without removing adhesive and/or applying new adhesive).

The urine collection device 400 can be in liquid communication with a vacuum pump or suction device 412. For example, the urine collection device 400 can be communicatively coupled to the suction device 412 by a vacuum tube 414. The suction device 412 can be used to extract urine from the urine collection device 400. One suitable non-limiting example of a suction device 412 is the DryDoc Vacuum Station, available from PureWick, Inc. As previously described, the vacuum tube 414 can be in liquid communication with the device 400. For example, a portion of the vacuum tube 414 can be received and retained by the receptacle 406 of the device 400 (see FIGS. 2 and 3).

Figure 5:
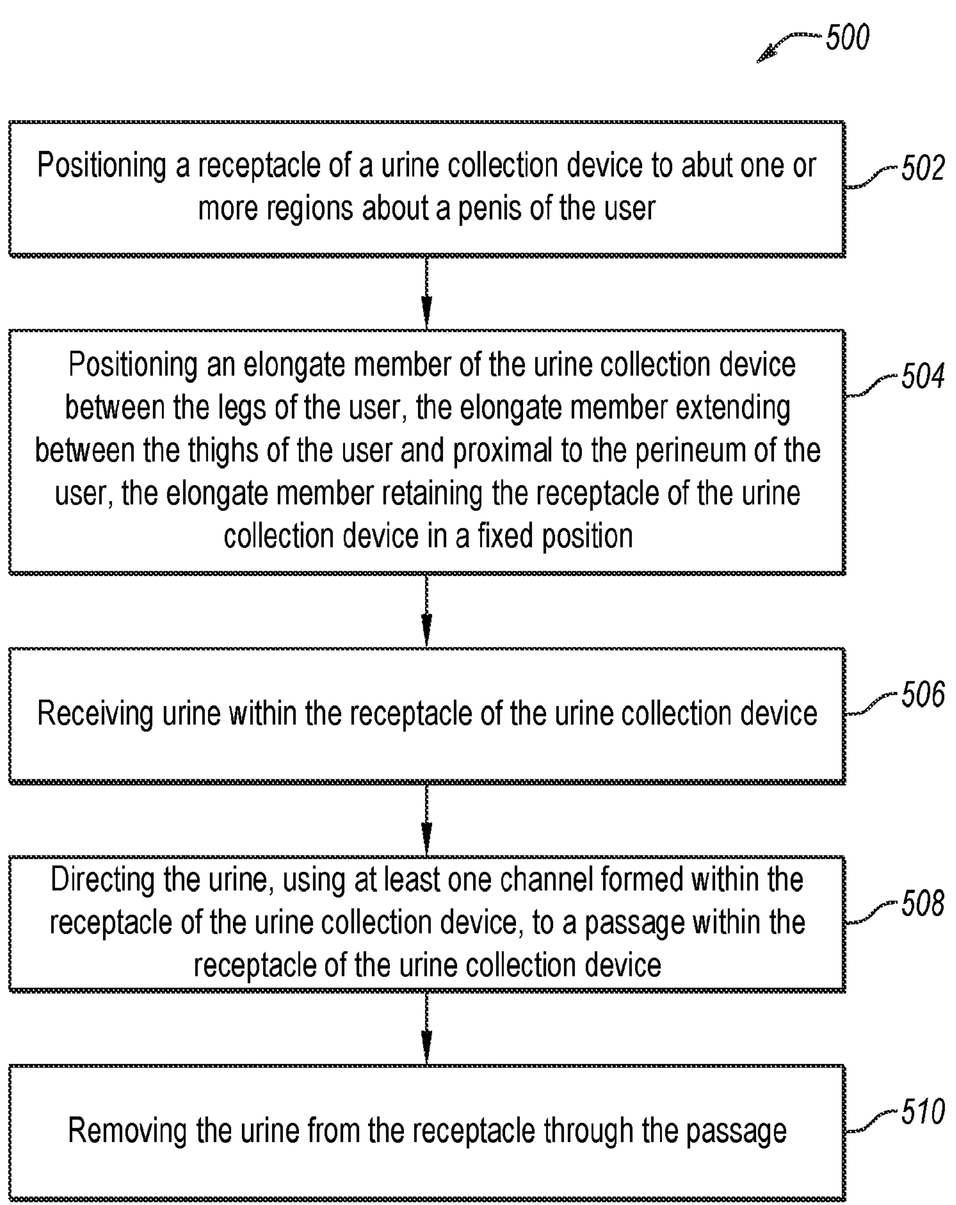
FIG. 5 is flow diagram of a method for using a urine collection device, according to an embodiment.

FIG. 5 is a flowchart illustrating a method 500 of using a urine collection device to collect urine from a user, according to an embodiment. The method 500 can include at least some of acts 502, 504, 506, 508, or 510. The method 500 is for illustrative purposes and, as such, at least one of the acts 502, 504, 506, 508, or 510 can be performed in a different order, split into multiple acts, modified, supplemented, combined, or omitted.

The method 500 optionally includes, at act 502, positioning a receptacle of a urine collection device to abut one or more regions about a penis of the user. Method 500 optionally further includes, at act 504, positioning an elongate member of the urine collection device between the legs of the user. In an embodiment, the elongate member can extend between the thighs of the user and proximal to the perineum of the user. By positioning the elongate member between the thighs of the user, the elongate member can retain the receptacle of the urine collection device in a fixed position relative to the user without requiring adhesives between the urine collection device and the user's skin. The elongate member can include a planar surface positioned near the distal end of the elongate member. The planar surface can be configured to abut the lower back or buttocks of the user and a support structure supporting the user (e.g., a chair, bed, etc.). The weight of the user can induce a downward force on the planar surface of the elongate member and thereby compress the planar surface between the user's body and the support structure. This compression can retain the receptacle of the urine collection device in a fixed position relative to the user by retaining the elongate member in a fixed position.

Method 500 further includes, at act 506, receiving urine within the receptacle of the urine collection device. The urine collection device can be the same or similar in structure and/or function to any of the urine collection devices described herein. For example, the receptacle can form or define at least one of a passage, one or more channels, and/or a collection region.

The method 500 also includes, at act 508, directing the urine, using at least one channel formed within the receptacle of the urine collection device, to a passage within the receptacle of the urine collection device. In an embodiment, the at least one channel directs, funnels, or otherwise guides urine to flow into a collection region. The collection region can be an area within the receptacle which temporarily houses or accumulates urine expelled within the receptacle.

The method 500 optionally includes, at act 510, removing the urine from the receptacle through the passage. In an embodiment, the passage can be in liquid communication with a vacuum pump or suction device. For example, a vacuum tube can be positioned within the passage such that urine accumulated within at the collection region can be removed via the tube.

The method 500 optionally includes positioning a material between the urine collection device and the user. In an embodiment, one or more fluid permeable layers can be positioned between the urine collection device and the user. For example, a first fluid permeable layer can be adhered or otherwise coupled to an inner surface of the receptacle. Additionally or alternatively, a second fluid permeable layer can be adhered or otherwise coupled to an inner surface of the elongate member.

While various embodiments of the urine collection system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. In addition, the specific configurations of the various components can also be varied. For example, the size and specific shape of the various components can be different than the embodiments shown, while still providing the functions as described herein.

The invention claimed is:

1. A urine collection device, comprising:

a receptacle defining an interior volume and configured to receive a penis of a user, the receptacle including at least one channel configured to direct urine within the interior volume toward a passage formed within the receptacle and an outlet in fluid communication with the passage, the passage being configured to extract urine from the receptacle; and an elongate member coupled to and extending from the receptacle opposite to the outlet, the elongate member having a distal end and a proximal end, the elongate member including a curved surface positioned between the proximal end and the distal end, a distal end region of the elongate member defining a substantially planar surface, the curved surface being sized and dimensioned for a portion of the elongate member to abut a perineum of the user with the substantially planar surface of the distal end region sized and dimensioned to receive a downward force on the planar surface from at least one of buttocks of the user or a lower back of the user to position the substantially planar surface between a support structure supporting the user and the at least one of buttocks of the user or a lower back of the user to retain the receptacle over the penis of the user without an adhesive or strap.

2. The urine collection device of claim 1, wherein the passage is in liquid communication with a suction device.

3. The urine collection device of claim 2, wherein the passage is configured to receive and retain a tube of the suction device.

4. The urine collection device of claim 1, further comprising a fluid permeable layer positioned within the volume, the fluid permeable layer overlaying the at least one internal channel and the passage.

5. The urine collection device of claim 4, wherein the fluid permeable layer is retained within the volume using an adhesive.

6. The urine collection device of claim 1, wherein the curved surface of the elongate member is configured to deform from a first curvature having a first radius to a second curvature having a second radius and retain the second curvature after being deformed.

7. The urine collection device of claim 1, wherein the elongate member retains the receptacle in a fixed position abutting one or more regions about the penis of the user when the elongate member is positioned between the thighs of the user and proximal to the perineum of the user.

8. The urine collection device of claim 7, wherein the receptacle is retained in the fixed position without adhering the urine collection device to the user.

9. The urine collection device of claim 1, wherein the distal end of the elongate member is wider than the proximal end of the elongate member.

10. The urine collection device of claim 1, further comprising a support layer overlaying at least a portion of the curved surface of the elongate member.

11. The urine collection device of claim 1, wherein the elongate member and the receptacle form a unitary structure.

12. The urine collection device of claim 1, wherein the at least one channel and the passage are in liquid communication with a collection region formed within the receptacle proximate to the elongate member, wherein the passage extends from the collection region that is proximate to the elongate member to the outlet that is opposite to the elongate member.

13. The urine collection device of claim 12, wherein the collection region is formed within the receptacle adjacent the elongate member.

14. The urine collection device of claim 12, wherein the collection region is disposed at a lower elevation than the at least one channel when the elongate member is abutting the perineum of the user.

15. The urine collection device of claim 1, wherein the receptacle defines a wall which extends around at least a portion of a periphery of the receptacle.

16. The urine collection device of claim 1, wherein the interior volume of the receptacle is sized and dimensioned to receive a penis of a user therein with the receptacle positioned around the penis of the user.

17. A method for transporting urine away from the body, the method comprising:

positioning a receptacle of a urine collection device to abut one or more regions about a penis of a user with the penis at least partially within an interior volume defined by the receptacle, the receptacle including at least one channel, a passage formed within the receptacle, and an outlet in fluid communication with the passage;

positioning an elongate member of the urine collection device between the legs of the user and a substantially planar surface of a distal end region of the elongate member between a support structure supporting the user and at least one of a buttocks of the user or a lower back of the user, the elongate member extending from the receptacle opposite to the outlet and having a curved portion between the substantially planar surface and the receptacle with the elongated member extending between the thighs of the user and at least proximate to the perineum of the user, the elongate member retaining the receptacle of the urine collection device in a fixed position to retain the receptacle over the penis of the user without an adhesive or strap;

receiving urine within the receptacle of the urine collection device;

directing the urine, using at least one channel formed within the receptacle of the urine collection device, to the passage within the receptacle of the urine collection device; and removing the urine from the receptacle through the passage and the outlet.

18. The method of claim 17, wherein a tube disposed within the passage and a suction device remove the urine from the receptacle through the passage and the outlet.

19. The method of claim 17, the urine collection device includes a material disposed between the receptacle and the user.

* * * * *